(12) United States Patent
Deisseroth et al.

(10) Patent No.: US 9,238,150 B2
(45) Date of Patent: *Jan. 19, 2016

(54) OPTICAL TISSUE INTERFACE METHOD AND APPARATUS FOR STIMULATING CELLS

(75) Inventors: Karl Deisseroth, Palo Alto, CA (US); Alexander Aravanis, San Diego, CA (US); Feng Zhang, Cambridge, MA (US); M. Bret Schneider, Portola Valley, CA (US); Jaimie M. Henderson, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 185 days.

This patent is subject to a terminal disclaimer.

(21) Appl. No.: 12/185,624

(22) Filed: Aug. 4, 2008

(65) Prior Publication Data

US 2009/0088680 A1    Apr. 2, 2009

Related U.S. Application Data

(63) Continuation-in-part of application No. 11/651,422, filed on Jan. 9, 2007, now Pat. No. 8,926,959, which is a continuation-in-part of application No. 11/459,636, filed on Jul. 24, 2006, now Pat. No. 8,906,360, and a continuation-in-part of application No. 12/041,628, filed on Mar. 3, 2008, now abandoned.

(60) Provisional application No. 60/953,920, filed on Aug. 3, 2007, provisional application No. 60/701,799, filed on Jul. 22, 2005, provisional application No. 60/904,303, filed on Mar. 1, 2007.

(51) Int. Cl.
*A61K 50/00* (2006.01)
*A61N 5/06* (2006.01)
*A61K 48/00* (2006.01)

(52) U.S. Cl.
CPC ............ *A61N 5/0622* (2013.01); *A61K 48/005* (2013.01); *A61K 48/0058* (2013.01); *A61K 48/0083* (2013.01); *A61N 5/0601* (2013.01); *A61N 5/062* (2013.01); *A61N 2005/0651* (2013.01)

(58) Field of Classification Search
CPC .................... A61N 5/0622; A61N 2005/0651; A61N 5/0601; A61N 5/062; A61K 48/005; A61K 48/0083; A61K 48/0058
See application file for complete search history.

(56) References Cited

U.S. PATENT DOCUMENTS

| | | | |
|---|---|---|---|
| 2,968,302 A | 1/1961 | Fry et al. | |
| 3,131,690 A | 5/1964 | Innis et al. | |
| 3,499,437 A | 3/1970 | Balamuth et al. | |
| 3,567,847 A * | 3/1971 | Price | 348/196 |
| 4,343,301 A | 8/1982 | Indech | |
| 4,559,951 A | 12/1985 | Dahl et al. | |
| 4,616,231 A | 10/1986 | Autrey et al. | |
| 4,865,042 A | 9/1989 | Umemura et al. | |
| 4,879,284 A | 11/1989 | Land et al. | |
| 5,032,123 A * | 7/1991 | Katz et al. | 606/15 |
| 5,041,224 A | 8/1991 | Ohyama et al. | |
| 5,082,670 A | 1/1992 | Gage et al. | |
| 5,249,575 A | 10/1993 | Di Mino et al. | |
| 5,267,152 A | 11/1993 | Yang et al. | |
| 5,290,280 A | 3/1994 | Daikuzono et al. | |
| 5,330,515 A | 7/1994 | Rutecki et al. | |
| 5,382,516 A | 1/1995 | Bush | |
| 5,445,608 A * | 8/1995 | Chen et al. | 604/20 |
| 5,460,950 A | 10/1995 | Barr et al. | |
| 5,460,954 A | 10/1995 | Lee et al. | |
| 5,470,307 A * | 11/1995 | Lindall | 604/20 |
| 5,495,541 A | 2/1996 | Murray et al. | |
| 5,520,188 A | 5/1996 | Hennige et al. | |
| 5,527,695 A | 6/1996 | Hodges et al. | |
| 5,550,316 A | 8/1996 | Mintz | |
| 5,641,650 A | 6/1997 | Turner et al. | |
| 5,703,985 A | 12/1997 | Owyang et al. | |

(Continued)

FOREIGN PATENT DOCUMENTS

| | | |
|---|---|---|
| CN | 1079464 A | 12/1993 |
| EP | 1 334 748 | 8/2003 |

(Continued)

OTHER PUBLICATIONS

Banghart et al., 2004, Nature Neuroscience, 7: 1381-1386.*
Mattson, 2000, Nature Reviews, 1: 120-12.*
Nagel et al., 2003, PNAS, USA, 100: 13940-13945.*
Blomer et al., 1997, Journal of Virology, 71: 6641-6649.*
Fitzsimons et al., 2002, Methods, 28: 227-236.*
Kocksis et al., 1982, Proc. R. Soc. Lond. B, 217: 77-87.*
Lee et al., 2003, Journal of Neurochemistry, 85: 1079-1088.*
Hodaie et al., 2002, Epilepsia, 43: 603-608.*
Axoclamp-2B Microelectrode claim theory and operation. accessed from https://physics.ucsd.edu/neurophysics/Manuals/Axon%20Instruments/Axoclamp-2B__Manual.pdf on Dec. 12, 2014.*
Babin et al. "Zebrafish models of human motor neuron diseases: Advantages and limitations." Progress in Neurobiology(2014); 118: pp. 36-58.*

(Continued)

*Primary Examiner* — Thaian N Ton
*Assistant Examiner* — Titilayo Moloye
(74) *Attorney, Agent, or Firm* — Bozicevic, Field & Francis LLP; Paula A. Borden

(57) ABSTRACT

In one example, a system electrically stimulates target cells of a living animal using an elongated structure, a modulation circuit and a light pathway such as provided by an optical fiber arrangement. The elongated structure is for insertion into a narrow passageway in the animal such that an end of the elongated structure is sufficiently near the target cells to deliver stimulation thereto. The modulation circuit is for modulating the target cells while the elongated structure is in the narrow passageway, where the modulation circuit is adapted to deliver viral vectors through the elongated structure for expressing light responsive proteins in the target cells. The light pathway is used for stimulating the target cells by delivering light to the light-responsive proteins in the target cells.

20 Claims, 11 Drawing Sheets

(56) References Cited

U.S. PATENT DOCUMENTS

| | | |
|---|---|---|
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A * | 8/1998 | Segalman et al. ............ 424/400 |
| 5,807,285 A | 9/1998 | Vaitekunas et al. |
| 5,816,256 A | 10/1998 | Kissinger et al. |
| 5,898,058 A | 4/1999 | Nichols |
| 5,939,320 A | 8/1999 | Littman et al. |
| 6,057,114 A | 5/2000 | Akong |
| 6,134,474 A | 10/2000 | Fischell et al. |
| 6,161,045 A | 12/2000 | Fischell et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,364,831 B1 | 4/2002 | Crowley |
| 6,377,842 B1 * | 4/2002 | Pogue et al. .................. 600/478 |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 * | 8/2003 | Gill ............................... 600/423 |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,696,722 B2 | 4/2014 | Deisseroth et al. |
| 8,815,582 B2 | 8/2014 | Deisseroth et al. |
| 8,906,360 B2 | 12/2014 | Deisseroth et al. |
| 2002/0164577 A1 | 11/2002 | Tsien et al. |
| 2003/0009103 A1 | 1/2003 | Yuste et al. |
| 2003/0026784 A1 | 2/2003 | Koch et al. |
| 2003/0088060 A1 | 5/2003 | Benjamin et al. |
| 2003/0097122 A1 | 5/2003 | Ganz et al. |
| 2003/0125719 A1 | 7/2003 | Furnish |
| 2004/0023203 A1 * | 2/2004 | Miesenbock et al. ............. 435/4 |
| 2004/0034882 A1 | 2/2004 | Vale et al. |
| 2004/0068202 A1 | 4/2004 | Hansson et al. |
| 2004/0076613 A1 | 4/2004 | Mazarkis et al. |
| 2005/0058987 A1 | 3/2005 | Shi et al. |
| 2005/0088177 A1 | 4/2005 | Schreck et al. |
| 2005/0107753 A1 * | 5/2005 | Rezai et al. ............. 604/288.04 |
| 2005/0202398 A1 | 9/2005 | Hegemann et al. |
| 2006/0057614 A1 | 3/2006 | Heintz |
| 2006/0100679 A1 | 5/2006 | DiMauro et al. |
| 2006/0106543 A1 | 5/2006 | Deco et al. |
| 2006/0155348 A1 | 7/2006 | deCharms |
| 2006/0161227 A1 | 7/2006 | Walsh et al. |
| 2006/0190044 A1 * | 8/2006 | Libbus et al. ..................... 607/3 |
| 2006/0206172 A1 | 9/2006 | DiMauro et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0054319 A1 | 3/2007 | Boyden et al. |
| 2007/0060915 A1 | 3/2007 | Kucklick |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0261127 A1 * | 11/2007 | Boyden et al. .................. 800/18 |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0145418 A1 | 6/2010 | Zhang et al. |
| 2010/0146645 A1 | 6/2010 | Vasar et al. |
| 2010/0190229 A1 | 7/2010 | Zhang et al. |

(56) References Cited

U.S. PATENT DOCUMENTS

| | | |
|---|---|---|
| 2010/0234273 A1 | 9/2010 | Boyden et al. |
| 2011/0021970 A1 | 1/2011 | Vo-Dinh et al. |
| 2011/0092800 A1 | 4/2011 | Yoo et al. |
| 2011/0105998 A1 | 5/2011 | Zhang et al. |
| 2011/0112179 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0172653 A1 | 7/2011 | Deisseroth et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0253261 A1 | 10/2012 | Poletto et al. |
| 2013/0030275 A1 | 1/2013 | Seymour et al. |
| 2013/0144359 A1 | 6/2013 | Kishawi et al. |
| 2015/0112411 A1 | 4/2015 | Beckman et al. |

FOREIGN PATENT DOCUMENTS

| | | |
|---|---|---|
| EP | 1873566 | 1/2008 |
| JP | 2006-295350 | 10/1994 |
| JP | 2010227537 A | 10/2010 |
| WO | WO 96/32076 | 10/1996 |
| WO | WO 00/27293 | 5/2000 |
| WO | WO 01-25466 | 4/2001 |
| WO | WO 03/016486 | 2/2003 |
| WO | WO 03/106486 A2 | 2/2003 |
| WO | WO 03-040323 | 5/2003 |
| WO | WO 03-084994 | 10/2003 |
| WO | WO 03-102156 | 12/2003 |
| WO | WO 2004/033647 | 4/2004 |
| WO | WO 2007-024391 | 3/2007 |
| WO | WO 2007-131180 | 11/2007 |
| WO | WO 2008/086470 | 7/2008 |
| WO | WO 2008/106694 | 9/2008 |
| WO | WO 2009/025819 | 2/2009 |
| WO | WO2009/119782 | 10/2009 |
| WO | WO 2009-131837 | 10/2009 |
| WO | WO 2010/006049 | 1/2010 |
| WO | WO 2010/011404 A3 | 1/2010 |
| WO | WO 2010/056970 | 5/2010 |
| WO | WO-2010123993 | 10/2010 |
| WO | WO 2011/066320 A3 | 6/2011 |
| WO | WO 2011-116238 A2 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 A2 | 10/2012 |
| WO | WO 2013/126521 | 8/2013 |
| WO | WO 2013/142196 | 9/2013 |

OTHER PUBLICATIONS

Thomas et al. "Progress and Problems With the Use of Viral Vectors for Gene." Nat Rev Genet. (2003);4(5):pp. 346-358.*

Sheikh et al. "Neurodegenerative Diseases: Multifactorial Conformational Diseases and Their Therapeutic Interventions." Journal of Neurodegenerative Diseases (2013); Article ID 563481: pp. 1-8.*

Suzuki et al."Stable Transgene Expression From HSV Amplicon ectors in the Brain: Potential Involvement of Immunoregulatory Signals." Molecular Therapy.(2008);16(10): pp. 1727-1736.*

Remarks by Robin Ali. http://www.vision-research.eu/index.php?id=696. acessed Jul. 24, 2015.*

Boyden, E.S., F. Zhang, E. Bamberg, G. Nagel, and K. Deisseroth, "*Millisecond-timescale, genetically targeted optical control of neural activity*," Nature Neuroscience, vol. 8, No. 9, pp. 1263-1268 (Aug. 14, 2005).

Zhang, F., L.P. Wang, E.S. Boyden, and K. Deisseroth, "*Channelrhodopsin-2 and optical control of excitable cells*," Nature Methods, vol. 3, No. 10, pp. 785-792 (Oct. 2006).

Aravanis, A. M. et al. "*An Optical Neural Interface: In Vivo Control of Rodent Motor Cortex with Integrated Fiberoptic and Optogenetic Technology*," Journal of Neural Engineering 4, pp. S143-S156 (2007).

Deisseroth, K., G. Feng, A.K. Majewska, G. Miesenbock, A. Ting, and M.J. Schnitzer, "*Next-generation optical technologies for illuminating genetically targeted brain circuits*," J Neurosci, 26(41): pp. 10380-10386 (Oct. 11, 2006).

Zhang F, Wang LP, Brauner M, Liewald JF, Kay K, Watzke N, Wood PG, Bamberg E, Nagel G, Gottschalk A, Deisseroth K., "*Multimodal fast optical interrogation of neural circuitry*," Nature. vol. 446, pp. 633-641 (Apr. 5, 2007).

Mayberg HS, Lozano AM, Voon V, McNeely HE, Seminowicz D, Hamani C, Schalb JM, Kennedy SH. "*Deep Brain Stimulation for Treatment-Resistant Depression*," Focus vol. VI, No. 1, pp. 143-154 (Winter 2008).

Schlaepfer TE, Cohen MX, Frick C, Kosel M, Brodesser D, Axmacher N, Joe AY, Kreft M, Lenartz D, Sturm V. "*Deep Brain stimulation to Reward Circuitry Alleviates Anhedonia in Refractory Major Depresion*," Neuropsychopharmacology 2008, 33, pp. 368-377.

Benabid AL. "*Future strategies to restore brain functions*," Conference proceedings from Medicine Meets Millennium: World Congress of Medicine and Health (2000).

Greenberg BD, Malone DA, Friehs GM, Rezai AR, Kubu CS, Malloy PF, Salloway SP, Okun MS, Goodman WK, Rasmussen SA. "*Three-year outcomes in deep brain stimulation for highly resistant obsessive-compulsive disorder*," Neuropsychopharmacology 31, pp. 2384-2393 (2006).

Singer HS, Szymanski S, Giuliano J, Yokoi F, A. Dogan S, Brasic JR, Zhou Y, Grace AA, and Wong DF. "*Elevated Intrasynaptic Dopamine Release in Tourette's Syndrome Measured by PET*," Am J Psychiatry. 159: 8, pp. 1329-1336. (Aug. 2002).

Ensell G, Banks DJ, Richards PR, Balachandra W, and Ewins DJ, Med & Bio. Engin. & Comput., "Silicon-based microelectrodes for neurophysiology, micromachined from silicon-on-insulator wafers," Med. Biol. Eng. Comput., 38, pp. 175-179 (2000).

Xiong et al., "Interregional connectivity to primary motor cortex revealed using MRI resting state images", Hum Brain Mapp, 1999, 8(2-3):151-156.

Fox et al., "A gene neuron expression fingerprint of C. elegans embryonic motor neurons", BMC Genomics, 2005, 6(42):1-23.

Nonet, "Visualization of synaptic specializations in live C. elegans with synaptic vesicle protein-GFP fusions", J. Neurosci. Methods, 1999, 89:33-40.

Synapse, Chapter 13, http://michaeldmann.net/mann13.html, downloaded Apr. 2014.

Berke, et al. "Addiction, Dopamine, and the Molecular Mechanisms of Memory", Molecular Plasticity, 2000, vol. 25: pp. 515-532.

Goshen et al. "Dynamics of Retrieval Strategies for Remote Memories", Cell, 2011, vol. 147: pp. 678-589.

Jimenez S.A & Maren S. et al/ "Nuclear disconnection within the amygdala reveals a direct pathway to fear", Learning Memory, 2009, vol. 16: pp. 766-768.

Ehrlich I. et al. "Amygdala inhibitory circuits and the control of fear memory", Neuron, 2009. Friedrich Meischer Institute, vol. 62: pp. 757-771.

Berndt et al. "Bi-stable neural state switches", Nature Neuroscience, 2009, vol. 12, No. 2: pp. 229-234.

Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.

Berndt et al., "Structure-Guided Transformation of Channelrhodopsin into a Light-Activated Chloride Channel", Science (Apr. 2014), 344(6182):420-424.

(56) References Cited

OTHER PUBLICATIONS

Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt 9):2585-2612.
Garrido et al., "A targeting motif involved in sodium channel clustering at the axonal initial segment", Science (Jun. 2003), 300(5628):2091-4.
Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al., "Virally mediated optogenetic excitation and inhibition of pain in freely moving nontransgenic mice", Nat Biotechnol., (Mar. 2014), 32(3):274-8.
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496(7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety" Nature (Apr. 2013), 496(7444):219-23.
Kokel et al., "Photochemical activation of TRPA1 channels in neurons and animals", Nat Chem Biol (Apr. 2013), 9(4):257-63.
Lammel et al., "Input-specific control of reward and aversion in the ventral tegmental area", Nature (Nov. 2012), 491(7423): 212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16(10):1161-5.
Mattis et al., "Principles for applying optogenetic tools derived from direct comparative analysis of microbial opsins", Nat Methods (Dec. 2011), 9(2):159-72.
Mourot et al., "Rapid Optical Control of Nociception with an Ion Channel Photoswitch", Nat Methods (Feb. 2012), 9(4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.
Towne et al., "Efficient transduction of non-human primate motor neurons after intramuscular delivery of recombinant AAV serotype 6", Gene Ther. (Jan. 2010), 17(1):141-6.
Towne et al., "Optogenetic control of targeted peripheral axons in freely moving animals", PLoS One (Aug. 2013), 8(8):e72691.
Towne et al., "Recombinant adeno-associated virus serotype 6 (rAAV2/6)-mediated gene transfer to nociceptive neurons through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5(177):177ps6.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila rhodopsin* cytoplasmic tail domain is required for maintenance of rhabdomere structure." The FASEB Journal, 2007, vol. 21, p. 449-455.
Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

Araki, et al. "Site-Directed Integration of the *cre* Gene Mediated by Cre Recombinase Using a Combination of Mutant *lox* Sites", Nucleic Acids Research, 2002, vol. 30, No. 19, pp. 1-8.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Basil et al. "Is There Evidence for Effectiveness of Transcranial Magnetic Stimulation in the Treatment of Psychiatric Disorders?" Psychiatry, 2005, pp. 64-69.
Bebbington et al., The use of vectors based on gene amplification for the expression of cloned genes in mammalian cells in "DNA cloning" vol. 3, Academic Press, New York, 1987.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.
Bocquet et al. "A prokaryotic proton-gated ion channel from the nicotinic acetylcholine receptor family." Nature Letters, 2007, vol. 445, p. 116-119.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cenatiempo "Prokaryotic gene expression in vitro: transcription-translation coupled systems", Biochimie, 1986, vol. 68(4): pp. 505-515.
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol. , 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cucchiaro et al., "Electron-Microsoft Analysis of Synaptic Input from the Perigeniculate Nucleus to A-Lamine of the Lateral Geniculate Nucleus in Cats", The Journal of Comparative Neurology, 1991, vol. 310, pp. 316-336.

(56) References Cited

OTHER PUBLICATIONS

Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994,vol. 265, pp. 255-258.
Dederen, et al. "Retrograde neuronal tracing with cholera toxin B subunit: comparison of three different visualization methods", Histochemical Journal, 1994, vol. 26, pp. 856-862.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-365.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their and electrophysiological monitoring in vivo", PNAS, 2004, vol. 101, No. 52, pp. 18206-18211.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Eisen, "Treatment of amyotrophic lateral sclerosis", Drugs Aging, 1999; vol. 14, No. 3, pp. 173-196.
Evanko "Optical excitation yin and yang" Nature Methods, 2007, 4:384.
Esposito et al. "The integrase family of tyrosine recombinases: evolution of a conserved active site domain" , Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Foster, "Bright blue times", Nature, 2005, vol. 433, pp. 698-699.
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from Bacillus subtilis DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.

Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat", Neuroscience, 1997, vol. 76, No. 3, pp. 689-706.
Gottesman et al."Bacterial regulation: global regulatory networks," Ann. Rev. Genet., 1984, vol. 18, pp. 415-441.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2. 1-9.2.10.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas rhodopsin*", Biophys. J. , 1991, vol. 60, pp. 1477-1489.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane," PNAS, 1993, vol. 90, pp. 3578-3582.
Hirase, et al. "Multiphoton stimulation of neurons", J Neurobiol, 2002, vol. 51, No. 3: pp. 237-247.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
International Search Report for International Application No. PCT/ US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Johnston et al. "Isolation of the yeast regulatory gene *GAL4* and analysis of its dosage effects on the galactose/melibiose regulon," PNAS, 1982, vol. 79, pp. 6971-6975.
Kandel, E.R.,et al. "Electrophysiology of Hippocampal Neurons: I. Sequential Invasion and Synaptic Organization," J Neurophysiol, 1961, vol. 24, pp. 225-242.

(56) References Cited

OTHER PUBLICATIONS

Kandel, E.R.,et al. "Electrophysiology of Hippocampal Neurons: II. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khossravani et al., "Voltage-Gated Calcium Channels and Idiopathic Generalized Epilepsies", Physiol. Rev., 2006, vol. 86: pp. 941-966.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kingston et al. "Transfection of DNA into Eukaryotic Cells," Supplement 63, Current Protocols in Molecular Biology, 1996, 9.1.1-9.1.11, 11 pages.
Kingston et al. "Transfection and Expression of Cloned DNA," Supplement 31, Current Protocols in Immunology, 1999, 10.13.1-1 0.13.9.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Landy, A. "Mechanistic and structural complexity in the site-specific recombination pathways of Int and FLP", Current Opinion in Genetics and Development, 1993, vol. 3, pp. 699-707.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Levitan et al. "Surface Expression of Kv1 Voltage-Gated K+ Channels is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.

Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of *FRT* sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Monje et al., "Irradiation Induces Neural Precursor-Cell Dysfunction", Natural Medicine, 2002, vol. 8, No. 9, pp. 955-962.
Mortensen et al. "Selection of Transfected Mammalian Cells," Supplement 86, Current Protocols in Molecular Biology, 1997, 9.5.1-09.5.19.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases" , Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al. "Functional Expression of a Directly Light-Gated Membrane Channel in Mammalian Retinal Neurons: A Potential Strategy for Restoring Light Sensitivity to the Retina After Photoreceptor Degeneration," Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.

(56) References Cited

OTHER PUBLICATIONS

Pear "Transient Transfection Methods for Preparation of High-Titer Retroviral Supernatants" Supplement 68, Current Protocols in Molecular Biology, 1996, 9.1 1 .I -9.1 1 .I 8.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Rivera et al., "BDNF-Induced TrkB Activation Down-Regulates the K+—Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.
Silver, et al. "Amino terminus of the yeast *GAL4* gene product is sufficient for nuclear localization" PNAS, 1984, vol. 81, No. 19: pp. 5951-5955.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Stark, et al. "Catalysis by site-specific recombinases," Trends Genet., 1992, vol. 8, No. 12: pp. 432-439.

Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Tsau et al. "Distributed Aspects of the Response to Siphon Touch in *Aplysia:* Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye et. al., "Amygdala circuitry mediating reversible and bidirectional control of anxiety", Nature, 2011, vol. 471(7338): pp. 358-362.
Tye et. al., Supplementary Materials: "An optically-resolved microcircuit for bidirectional anxiety control", Nature, 2011, vol. 471(7338): pp. 358-362.
Ulmanen, et al. "Transcription and translation of foreign genes in *Bacillus subtilis* by the aid of a secretion vector," Journal of Bacteriology, 1985, vol. 162, No. 1: pp. 176-182.
Vanin, et al. "Development of high-titer retroviral producer cell lines by using Cre-mediated recombination," Journal of Virology, 1997, vol. 71, No. 10: pp. 7820-7826.
Wagner, "Noninvasive Human Brain Stimulation", Annual Rev. Biomed. Eng. 2007. 9:19.1-19.39.
Ward, et al. "Construction and characterisation of a series of multicopy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et al. "Direct-current Nanogenerator Driven by Ultrasonic Waves," Science, 2007, vol. 316, pp. 102-105.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human $\beta,\beta$-Carotene-15, 15'-Dioxygenase that is Highly Expressed in the Retinal Pigment Epithelium", Genomics, 2001, vol. 72: pp. 193-202.
Yizhar et. al., "Neocortical excitation/inhibition balance in information processing and social dysfunction", Nature, 2011, vol. 477, pp. 171-178; and Supplemental Materials; 41 pages.
Yoshimura, et al. "Excitatory cortical neurons form fine-scale functional networks", Nature, 2005, vol. 433: pp. 868-873.

(56) References Cited

OTHER PUBLICATIONS

Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Red-Shifted Optogenetic Excitation: a Tool for Fast Neural Control Derived from Volvox carteri", Nature Neurosciences, 2008, vol. 11, No. 6, pp. 631-633.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Carter, Matthew E., et al. "Optogenetic investigation of neural circuits in vivo", Trends Mol. Med. 2011, 2011, vol. 17, No. 4, pp. 197-206.
Kramer, Richard H., et al. "New photochemical tools for controlling neuronal activity", Curr Opin Neurobiol, 2009, vol. 19, No. 5, pp. 544-552.
Rein, Martin L., et al., "The optogenetic (r)evolution", Mol Genet Genomics, 2012, vol. 287, pp. 95-109.
Gradinaru et al., "Targeting and readout strategies for fast optical neural control in vitro and in vivo", J Neuroscience, 2007, 27(52):14231-14238.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Gradinaru, et al., Molecular and Cellular Approaches for Diversifying and Extending Optogenetics, Cell, 2010, vol. 141, No. 1, pp. 154-165.
Li et al., "Surface Expression of Kv1 Channels is Governed by a C-Terminal Motif", J. Biol. Chem. (2000), 275(16):11597-11602.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Deisseroth, et al., "Controlling the Brain with Light", Scientific American, 2010, vol. 303, pp. 48-55.
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Sineshchekov, et al., "Two Rhodopsins Mediate Phototaxis to Low and High Intensity Light in Chlamydomas Reinhardtil", PNAS, 2002, vol. 99, No. 13, pp. 8689-8694.
Tønnese, et al., "Optogenetic Control of Epileptiform Activity", PNAS, 2009, vol. 106, No. 29, pp. 12162-12167.
Pear "Transient Transfection Methods for Preparation of High-Titer Retroviral Supernatants" Supplement 68, Current Protocols in Molecular Biology, 1996, 9.1 1 .1-9.1 1.1 8.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Gonzalez, et al. "Cell-Based Assays and Instrumentation for Screening Ion-Channel Targets", DDT, 1999, vol. 4, No. 9, pp. 431439.
Natochin, et al. "Probing rhodopsin-transducin interaction using *Drosophila* Rh1-bovine rhodopsin chimeras," Vision Res., 2006, vol. 46, No. 27: pp. 4575-4581.
Hikida et al., "Increased sensitivity to cocaine by cholinergic cell ablation in nucleus accumbens", PNAS, Nov. 2001, 98(23): 13351-13354.
Hikida et al., "Acetylcholine enhancement in the nucleus accumbens prevents addictive behaviors of cocaine and morphine", PNAS, May 2003, 100(10):6169-6173.
Kitabatake et al., "Impairment of reward-related learning by cholinergic cell ablation in the striatum", PNAS, Jun. 2003, 100(13):7965-7970.
Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004, pp. 750-769.
Fiala et al., "Optogenetic approaches in neuroscience", Current Biology, Oct. 2010, 20(20):R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem,2007,87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *Drosophila* larvae", Current Biology, Sep. 2006, 16(17):1741-1747.
Airan, et al., "Temporally Precise in vivo Control of Intracellular Signaling", 2009, Nature, vol. 458, No. 7241, pp. 1025-1029.
Braun, "Two Light-activated Conductances in the Eye of the Green Alga Volvox carteri", 1999, Biophys J., vol. 76, No. 3, pp. 1668-1678.
Cardin, et al. "Driving Fast spiking Cells Induces Gamma Rhythm and Controls Sensory Responses", 2009, Nature, vol. 459, vol. 7247, pp. 663-667.
Deisseroth et al., "Excitation-neurogenesis Coupling in Adult Neural Stem/Progenitor Cells", 2004, Neuron, vol. 42, pp. 535-552.
Ernst, et al. "Photoactivation of Channelrhodopsin", 2008, vol. 283, No. 3, pp. 1637-1643.
Genbank Accession No. DQ094781 (Jan. 15, 2008).
Gradinaru, et al. "ENpHR: a Natronomonas Halorhodopsin Enhanced for Optogenetic Applications", 2008, Brain Cell Biol., vol. 36 (1-4), pp. 129-139.
Herlitze, et al., "New Optical Tools for Controlling Neuronal Activity", 2007, Curr Opin Neurobiol, vol. 17, No. 1, pp. 87-94.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
McAllister, "Cellular and Molecular Mechanisms of Dendrite Growth", 2000, Cereb Cortex, vol. 10, No. 10, pp. 963-973.
Pape, et al., "Plastic Synaptic Networks of the Amygdala for the Acquisition, Expression, and Extinction of Conditioned Fear", 2010, Physiol Rev, vol. 90, pp. 419-463.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Ritter, et al., "Monitoring Light-induced Structural Changes of Channelrhodopsin-2 by UV-Visable and Fourier Transform Infared Spectroscopy", 2008, The Journal of Biological Chemistry, vol. 283, No. 50, pp. 35033-35041.
Sajdyk, et al., "Excitatory Amino Acid Receptors in the Basolateral Amygdala Regulate Anxiety Responses in the Social Interaction Test", Brain Research, 1997, vol. 764, pp. 262-264.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.

(56) References Cited

OTHER PUBLICATIONS

Swiss-Prot_Q2QCJ4, Opsin 1, Oct. 31, 2006, URL: http://www.ncbi.nlm.nig.gov/protein/Q2QCJ4.
"SubName: Full=Channelrhodopsin-1", retrieved from EBI accession No. UNIPROT: B4Y103. Database accession No. B4Y103. Sep. 23, 2008.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.
Lanyi et al. "The primary structure of a Halorhodopsin from *Natronobacterium Pharaonis*" Journal of Biological Chemistry 1990, vol. 265, No. 3, p. 1253-1260.
Hofherr et al. "Selective Golgi export of Kir2.1 controls the stoichiometry of functional Kir2.x channel heteromers" Journal of Cell Science, 2005, vol. 118, p. 1935-1943.
Loetterle, et al., "Cerebellar Stimulation: Pacing the Brain", American Journal of Nursing, 1975, vol. 75, No. 6, pp. 958-960.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"*N. pharaonis halorhodopsin* (hop) gene, complete cds.", XP002704883, retrieved from EBI accession No. EMBL: J05199. Database accession No. J05199. Nov. 22, 1990.
"Subname: Fluu=Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Balint, et al., "The Nitrate Transporting Photochemical Reaction Cycle of the Pharaonis Halorhodopsin", Biophysical Journal, 2004, vol. 86, pp. 1655-1663.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.
Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential for use in research and the clinic", Brain Stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.

Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Pinkham et al., "Neural bases for impaired social cognition in schizophrenia and autism spectrum disorders", Schizophrenia Research, 2008, vol. 99, pp. 164-175.
Sohal et al., "Parvalbumin neurons and gamma rhythms enhance cortical circuit performance", Nature, 2009, vol. 459, No. 7247, pp. 698-702.
Yizhar et al., "Optogenetics in neural systems", Neuron Primer, 2011, vol. 71, No. 1, pp. 9-34.
Cazillis et al., "VIP and PACAP induce selective neuronal differentiation of mouse embryonic stem cells", Eur J Neurosci, 2004, 19(4):798-808.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Tye, et al. "Optogenetic investigation of neural circuits underlying brain disease in animal models," Nature Reviews Neuroscience (Mar. 2012), 13(4):251-266.
Arenkiel, et al. "In vivo light-induced activation of neural circuitry in transgenic mice expressing Channelrhodopsin-2", Neuron, 2007, 54:205-218.
Milella et al. "Opposite roles of dopamine and orexin in quinpirole-induced excessive drinking: a rat model of psychotic polydipsia" Psychopharmacology, 2010, 211:355-366.
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse Ren-2 gene", Nature, 1990, vol. 344, pp. 541-544.
Mullins et al., "Expression of the DBA/2J Ren-2 gene in the adrenal gland of transgenic mice", EMBO, 1989, vol. 8, pp. 4065-4072.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Written opinion of PCT Application No. PCT/US2011/059383 (May 9, 2012).
Peterlin, et al. "Optical probing of neuronal circuits with calcium indicators," PNAS, 2000, vol. 97, No. 7: pp. 3619-3624.

(56) References Cited

OTHER PUBLICATIONS

Shibasaki et al., "Effects of body temperature on neural activity in the hippocampus: Regulation of resting membrane potentials by transient receptor potential vanilloid 4," The Journal of Neuroscience, 2007, 27(7):1566-1575.

Takahashi, et al., "Induction of Pluripotent Stem Cells from Mouse Embryonic and Adult Fibroblast Cultures by Defined Factors", 2006, Cell, vol. 126, pp. 663-676.

Davis; "The many faces of epidermal growth factor repeats," The New Biologist; vol. 2, No. 5, pp. 410-419 (1990).

De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).

EBI accession No. UNIPROT: A7U0Y6; "SubName: Full=Bacteriorhodopsin"; (Aug. 10, 2010).

Ihara, et al.; "Evolution of the Archaeal Rhodopsins: Evolution Rate Changes by Gene Duplication and Functional Differentiation"; J. Mol. Biol.; vol. 285, pp. 163-174 (1999).

Kaiser; "Clinical research. Death prompts a review of gene therapy vector"; Science; 317(5838):580 (Aug. 3, 2007).

Kay; "State-of-the-art gene-based therapies: the road ahead"; Nature Reviews Genetics; vol. 12, pp. 316-328 (May 2011).

Singer; "Light Switch for Bladder Control"; Technology Review; pp. 1-2 (Sep. 14, 2009).

Skolnick, et al.; "From genes to protein structure and function: novel applications of computational approaches in the genomic era"; Trends Biotechnol; vol. 18, No. 1, pp. 34-39 (Jan. 2000).

Soofiyani, et al.; "Gene Therapy, Early Promises, Subsequent Problems, and Recent Breakthroughs"; Advanced Pharmaceutical Bulletin; vol. 3, No. 2, pp. 249-255 (2013).

Brewin; "The Nature and Significance of Memory Disturbance in Posttraumatic Stress Disorder"; Ann. Rev. Clin. Psychol.; vol. 7, pp. 203-227 (2011).

Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).

Samuelson; "Post-traumatic stress disorder and declarative memory functioning: a review"; Dialogues in Clinical Neuroscience; vol. 13, No. 3, pp. 346-351 (2011).

Babin et al., "Zebrafish Models of Human Motor Neuron Diseases: Advantages and Limitations", Progress in Neurobiology (2014), 118:36-58.

Santana et al., "Can Zebrafish Be Used as Animal Model to Study Alzheimer's Disease?" Am. J. Neurodegener. Dis. (2012), 1(1):32-48.

Sheikh et al., "Neurodegenerative Diseases: Multifactorial Conformational Diseases and Their Therapeutic Interventions", Journal of Neurodegenerative Diseases (2013), Article ID 563481:1-8.

Suzuki et al., "Stable Transgene Expression from HSV Amplicon Vectors in the Brain: Potential Involvement of Immunoregulatory Signals", Molecular Therapy (2008), 16(10):1727-1736.

Thomas et al., "Progress and Problems with the Use of Viral Vectors for Gene", Nat. Rev. Genet. (2003), 4(5):346-358.

Ali; "Gene and stem cell therapy for retinal disorders"; vision-research.en—The Gateway to European Vision Research; accessed from http://www.vision-research.eu/index.php?id=696, 10 pages (accessed Jul. 24, 2015).

Mueller, et al.; "Clinical Gene Therapy Using Recombinant Adeno-Associated Virus Vectors"; Gene Therapy; vol. 15, pp. 858-863 (2008).

Asano, et al.; "Optically Controlled Contraction of Photosensitive Skeletal Muscle Cells"; Biotechnology & Bioengineering; vol. 109, No. 1, pp. 199-204 (Jan. 2012).

Bruegmann, et al.; "Optogenetic control of heart muscle in vitro and in vivo"; Nature Methods; vol. 7, No. 11, pp. 897-900(Nov. 2010).

Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).

Genbank Accession No. AAG01180.1; Idnurm, et al.; pp. 1 (Mar. 21, 2001).

Genbank Accession No. ABT17417.1; Sharma, et al.; pp. 1 (Aug. 15, 2007).

Genbank Accession No. BAA09452.1; Mukohata et al.; pp. 1 (Feb. 10, 1999).

Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).

Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).

Han, et a.; "Virogenetic and optogenetic mechanisms to define potential therapeutic targets in psychiatric disorders"; Neuropharmacology; vol. 62, pp. 89-100 (2012).

Zhang, et al.; "Optogenetic interrogation of neural circuits: Technology for probing mammalian brain structures"; Nature Protocols; vol. 5, No. 3, pp. 439-456 (Mar. 1, 2010).

Han, et al., "Millisecond-Timescale Optical Control of Neural Dynamics in the Nonhuman Primate Brain"; Neuron; vol. 62, pp. 191-198 (Apr. 30, 2009).

Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).

\* cited by examiner

OPTICAL TISSUE INTERFACE METHOD AND APPARATUS FOR STIMULATING CELLS

RELATED PATENT DOCUMENTS

This patent document claims the benefit, under 35 U.S.C. § 119(e), of U.S. Provisional Patent Application Ser. No. 60/953,920, entitled Optical Tissue Interface Method and Apparatus for Stimulating Cells and filed on Aug. 3, 2007; this patent application, including the Appendix therein, is fully incorporated herein by reference.

This patent document also claims priority, as a CIP under 35 U.S.C. § 120, to the following patent documents which are also individually incorporated by reference: U.S. patent application Ser. No. 11/651,422, filed on Jan. 9, 2007 and entitled, System for Optical Stimulation of Target Cells), which is a CIP of U.S. patent application Ser. No. 11/459,636, filed on Jul. 24, 2006 and entitled, Light-Activated Cation Channel and Uses Thereof, which claims the benefit of U.S. Provisional Application No. 60/701,799, filed Jul. 22, 2005; and U.S. patent application Ser. No. 12/041,628, filed on Mar. 3, 2008 and entitled, Systems, Methods And Compositions For Optical Stimulation Of Target Cells, which claims the benefit of U.S. Provisional Application No. 60/904,303, filed on Mar. 1, 2007.

GOVERNMENT RIGHTS

This invention was made with Government support under OD000616 awarded by the National Institutes of Health. The Government has certain rights in this invention.

FIELD OF THE INVENTION

The present invention relates generally to systems and/or methods for stimulating target cells optically and more particularly to an optical neural interface, system and method for delivery of genetic modifiers and optical stimulus to target cells.

BACKGROUND AND OVERVIEW

The stimulation of various cells of the body has been used to produce a number of beneficial effects. One method of stimulation involves the use of electrodes to introduce an externally generated signal into cells. For example, in connection with electrode-based brain stimulation techniques, the distributed nature of neurons may be responsible for a given mental process. Also, different types of neurons reside close to one another such that only certain cells in a given region of the brain may be activated while performing a specific task. Not only do heterogeneous nerve tracts move in parallel through tight spatial confines, but the cell bodies themselves may exist in mixed, sparsely embedded configurations. This distributed manner of processing is an issue in attempts to understand canonical order within the Central Nervous System (CNS), and can make neuromodulation a difficult therapeutic endeavor. Due to this architecture of the brain, there are issues concerning use of electrode-based stimulation which is relatively indiscriminate with regards to the underlying physiology of the neurons that they stimulate. Instead, physical proximity of the electrode poles to the neuron is often the single largest determining factor as to which neurons will be stimulated.

Electrode placement and mechanical stability can also be an important influence on the effectiveness of electrode stimulation since location often dictates which neurons will be stimulated, and flawed location/stability can result in lead migration of the electrodes from the targeted area. Moreover, after a period of time within the body, electrode leads frequently become encapsulated with glial cells, raising the effective electrical resistance of the electrodes, and hence the electrical power delivery required to reach targeted cells. Compensatory increases in voltage, frequency or pulse width, however, may spread electrical current and result in increases in unintended stimulation of additional cells.

In connection with work by the named inventor(s) of this patent document, recently discovered techniques allow for stimulation of cells resulting in the rapid depolarization of cells (e.g., in the millisecond range). One method of stimulus uses photosensitive bio-molecular structures to stimulate target cells in response to light. For instance, light activated proteins can be used to control the flow of ions through cell membranes. Ion channels and ion pumps are cell-membrane proteins that control the transport of positively or negatively charged ions (e.g., sodium, potassium and chloride) across the cell membrane. Ion channels play an important part of various animal and human functions including signaling and metabolism. Using optically responsive ion channels or pumps to facilitate or inhibit the flow of positive or negative ions through cell membranes, the cell can be briefly depolarized, depolarized and maintained in that state, or hyperpolarized. Neurons are an example of a type of cell that uses the electrical currents created by depolarization to generate communication signals (i.e., nerve impulses). Other electrically excitable cells include skeletal muscle, cardiac muscle, and endocrine cells.

Various techniques can be used to control the depolarization of cells such as neurons. Neurons use rapid depolarization to transmit signals throughout the body and for various purposes, such as motor control (e.g., muscle contractions), sensory responses (e.g., touch, hearing, and other senses) and computational functions (e.g., brain functions). Thus, the control of the depolarization of cells can be beneficial for a number of different purposes, including (but not limited to) psychological therapy, muscle control and sensory functions. For further details on specific implementations of photosensitive bio-molecular structures and methods, reference can be made to "Millisecond-Timescale, Genetically Optical Control of Neural Activity", *Nature Neuroscience* 8, 1263-1268 (2005). This reference discusses use of blue-light-activated ion channel channelrhodopsin-2 (ChR2) to cause calcium (Ca++)-mediated neural depolarization, and is fully incorporated herein by reference. Other applicable light-activated ion channels include halorhodopsin (NpHR), in which amber light affects chloride (Cl−) ion flow so as to hyperpolarize neuronal membrane, and make it resistant to firing.

SUMMARY

Various aspects of the invention address the above-discussed issues and others as would become apparent from the discussion that follows.

According to one embodiment, the present invention is directed to a system for electrically stimulating targeted excitable cells of a living animal using light to alter the electrical behavior of the cells.

According to one embodiment, a system electrically stimulates targeted excitable cells of a living animal by using an elongated structure, a modulation circuit and a light pathway such as provided by an optical fiber arrangement. The elongated structure is for insertion into a narrow passageway in the animal such that an end of the elongated structure is sufficiently near the target cells to deliver stimulation thereto. The modulation circuit is for modulating the target cells while the elongated structure is in the narrow passageway, where the modulation circuit is adapted to deliver viral vectors through the elongated structure for expressing light responsive proteins in the target cells. The light pathway is used for stimulating the target cells by delivering light to the light-responsive proteins in the target cells.

According to another embodiment, a method electrically stimulates target cells of a living animal in vivo. An elongated structure is inserted into a narrow passageway in the animal such that an end of the structure is sufficiently near the target cells to deliver stimulation thereto. While the elongated structure is in the narrow passageway, viral vectors are delivered through the elongated structure for expressing light responsive proteins in the target cells. After delivering the viral vectors, an optical fiber is inserted through the elongated structure. The target cells are stimulated by using the optical fiber to deliver light to expressed light responsive proteins in the target cells.

According to one embodiment, an elongated structure is inserted into a narrow passageway in an animal for modulating of the activity of electrically-excitable cells. Growth of light-gated ion channels or pumps is induced in the membrane of a nerve cell located at a selected target within the body. At least one flash of light is directed upon the light-activated proteins so as to modulate the function of the target or surrounding cells.

According to one embodiment, an arrangement is implemented with an elongated structure inserted into a narrow passageway in an animal for modulating of the activity of electrically-excitable cells and for actively growing light-gated ion channels or pumps in the membrane of a nerve cell located at a selected target within the body. A light source is used for directing at least one flash of light upon the light-activated proteins so as to modulate the function of the target or surrounding cells.

According to one embodiment, a system electrically stimulates target cells of a living animal in vivo. The system includes an elongated structure for insertion into a narrow passageway in the animal such that an end of the elongated structure is sufficiently near the target cells to deliver stimulation thereto. A modulation circuit is included for modulating the target cells while the elongated structure is in the narrow passageway, the modulation circuit including means for delivering viral vectors through the elongated structure for expressing light responsive proteins in the target cells. An optical fiber arrangement is included for stimulating the target cells by delivering light to the light-responsive proteins in the target cells.

According to one embodiment, a system electrically stimulates target neurons in a brain in vivo via the skull. The system has an elongated structure having two ends and a passage extending between the ends. The elongated structure is sufficiently small for insertion through the skull and into the brain. A mount secures the elongated structure to the skull. A reservoir holds viral vectors for expressing at least one of ChR2 and NpHR in the target cells. A delivery device moves the viral vectors from the reservoir through the passage and to the target neurons. An optical fiber light-delivery arrangement includes an optical fiber for insertion through the passage and a light generator for sourcing light through the optical fiber to stimulate the target cells and to activate the at least one of ChR2 and NpHR expressed in the target cells. The light delivered through the optical fiber illuminates an area of the brain in which the target neurons are located.

The above summary is not intended to describe each illustrated embodiment or every implementation of the present invention.

BRIEF DESCRIPTION OF THE DRAWINGS

The invention may be more completely understood in consideration of the detailed description of various embodiments of the invention that follows in connection with the accompanying drawings, in which.

Figure 1A:
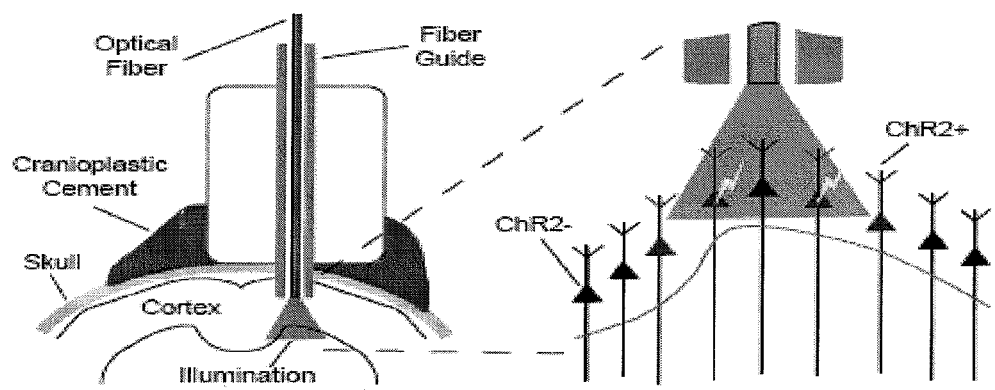
FIGS. 1A and 1B are diagrams of respective arrangements for application to mammalian skulls, each arrangement including an optical neural interface according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is directed to practical application of a variety of optically-based stimulus systems, and the invention has been found to be particularly suited for use in systems and methods dealing with stimulation of target cells using a cannula (a tube for insertion into a body cavity or into a duct or vessel) to deliver optically responsive genetic modifiers and optical stimulus to target cells. While the present invention is not necessarily limited to such applications, various aspects of the invention may be appreciated through a discussion of various examples using this context.

Recently discovered techniques allow for stimulation of cells resulting in the rapid depolarization of cells (e.g., in the millisecond range). Such techniques can be used to control the depolarization of cells such as neurons. Neurons use rapid depolarization to transmit signals throughout the body and for various purposes, such as motor control (e.g., muscle contractions), sensory responses (e.g., touch, hearing, and other senses) and computational functions (e.g., brain functions). Thus, the control of the depolarization of cells can be beneficial for a number of different biological applications, among others including psychological therapy, muscle control and sensory functions. For further details on specific implementations of photosensitive bio-molecular structures and methods, reference can be made to the above-referenced patent documents by Karl Deisseroth et al., which are fully incorporated herein by reference. These references discuss use of blue-light-activated ion-channel channelrhodopsin-2 (ChR2) to cause calcium (Ca++)-mediated neural depolarization. Other applicable light-activated ion channels include, for example, halorhodopsin (NpHR) in which amber light affects chloride (Cl−) ion flow so as to hyperpolarize aneuronal membrane, and make it resistant to firing.

Certain aspects of the present invention are directed to stimulating target cells via optogenetic excitation and/or to optogenetic stabilization. Optogenetic excitation refers to a combined optical and genetic approach that increases the depolarization rate of the targeted cell population. While not necessarily limited to this application (or agent), one approach to achieving such increases involves expression of ChR2 in targeted cells, and blue light, emitted for example, from a surgically implanted hardware device, is flashed to trigger depolarization. Optogenetic stabilization refers to a combined optical and genetic approach that decreases the depolarization rate of the targeted cell population. One approach to achieving such decreases is to cause NpHR to be expressed in targeted cells. Yellow light emitted for example, from a surgically implanted hardware device, is provided to hyperpolarize the membrane and prevent depolarization. Optogenetic stabilization is not necessarily limited to any particular genetic agent and may apply to other appropriate optogenetic agents as well as to variations on the delivery of light thereto.

Consistent with one example embodiment of the present invention, a system is implemented for providing in vivo stimulus (e.g., via optogenetic excitation and/or to optogenetic stabilization) to target cells. The system provides an elegant solution for both modifying the target cells to be optically responsive and stimulating the target cells optically. One end of a cannula may be stereotactically or otherwise guided near the target cells. Viral vectors or other cell modifiers are inserted through the other end of the cannula to modify the target cells to be optically responsive. The cannula is then used to guide an optical delivery device, such as fiber optics, to the same site that the viral vectors were delivered. Optical stimulus is provided to the target cells using the optical delivery device. Generally, these and other applications are discussed herein in the context of live animals; however, other applications (e.g., postmortem or otherwise) are also envisioned.

For the delivery of light to photo-sensitive neurons and other cell types, there are several different possible light sources, each having its own benefits with respect to power, wavelength, heat production, optical coupling, size, and cost. A few example light sources include, but are not limited to, lasers (gas, crystal, and solid-state) and light-emitting diodes (LEDs). Optical fibers have many properties that make them beneficial for the delivery of light deep within tissue such as the brain. They are thin, light-weight, flexible, and transmit light with negligible loss over short distances. In addition to single optical fibers, fiber bundles or arrays of optical fibers can be useful for light delivery depending on the size and location of the tissue targeted. For some applications direct light delivery an LED may be preferred. For example, treatment of cortical brain tissue or heart tissue LED illumination may be efficacious.

In one embodiment, a system that includes a power supply, control circuit, light source, and light conduit, could be implanted. This can be useful for minimizing infection and improving patient convenience. In order to facilitate such implantation, the light source/housing/power supply "box" can be designed on the order of the largest current neuro-stimulators. The supply box can also be designed to either be rechargeable or to have a long battery life (e.g., 3 years or more).

According to one embodiment of the presenting invention, an implantable cylindrical structure (e.g., a cannula or a catheter) includes multiple parallel fibers terminating around the circumference of a cylindrical structure, over a span of several millimeters. This allows for "steering" of light to various portions and allows intensity control by activation of more or fewer fibers. Such multiplexing of light through multiple fibers can also be useful for spatial control of light delivery.

One such device can be reinforced for protection of the light guides so as to survive clumsy handling by surgeons and the bending/buckling stresses encountered inside a mobile animal/human body. In one instance, the device can be arranged with optical connectors that allow replacement of the light guide.

One such device may also be arranged to facilitate the integration of electrical recording with optical stimulation. In a particular instance this is accomplished using different populations of fibers, and an electrical recording component which could either be an array of microelectrodes (a la Cyberkinetics/Utah) or larger macroelectrodes to record local field potentials.

According to another embodiment, microfluidic integration can be useful, given the potential need for "booster" injections of vector. This can be particularly useful for delivery mechanisms that require periodic delivery, such as adenovirus-based delivery.

According to one embodiment of the present invention, the cannula may be fixed to a skull (mammalian or otherwise) using adhesive, or other suitable attachment mechanisms, prior to the delivery of the (ChR2/NpHR) solution. This can be useful for maintaining the location for the end of the cannula located near the target cells during the entire procedure. The solution may be administered directly through the cannula or through a separate deliver lumen or tube that may be inserted through the cannula. The first lumen may be subsequently removed and fiber optics or a lens and mirror arrangement may be inserted into the lumen.

Figure 1A:
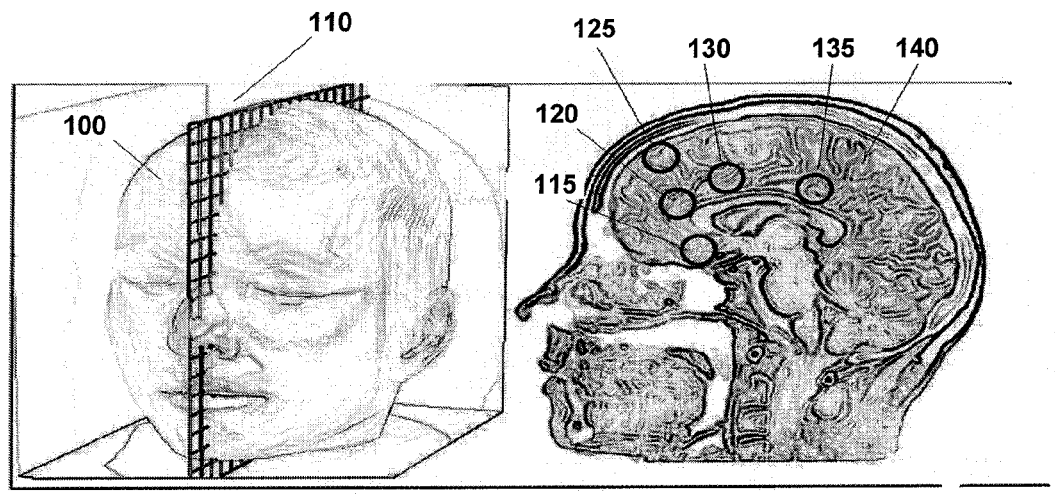
Figure 1B:
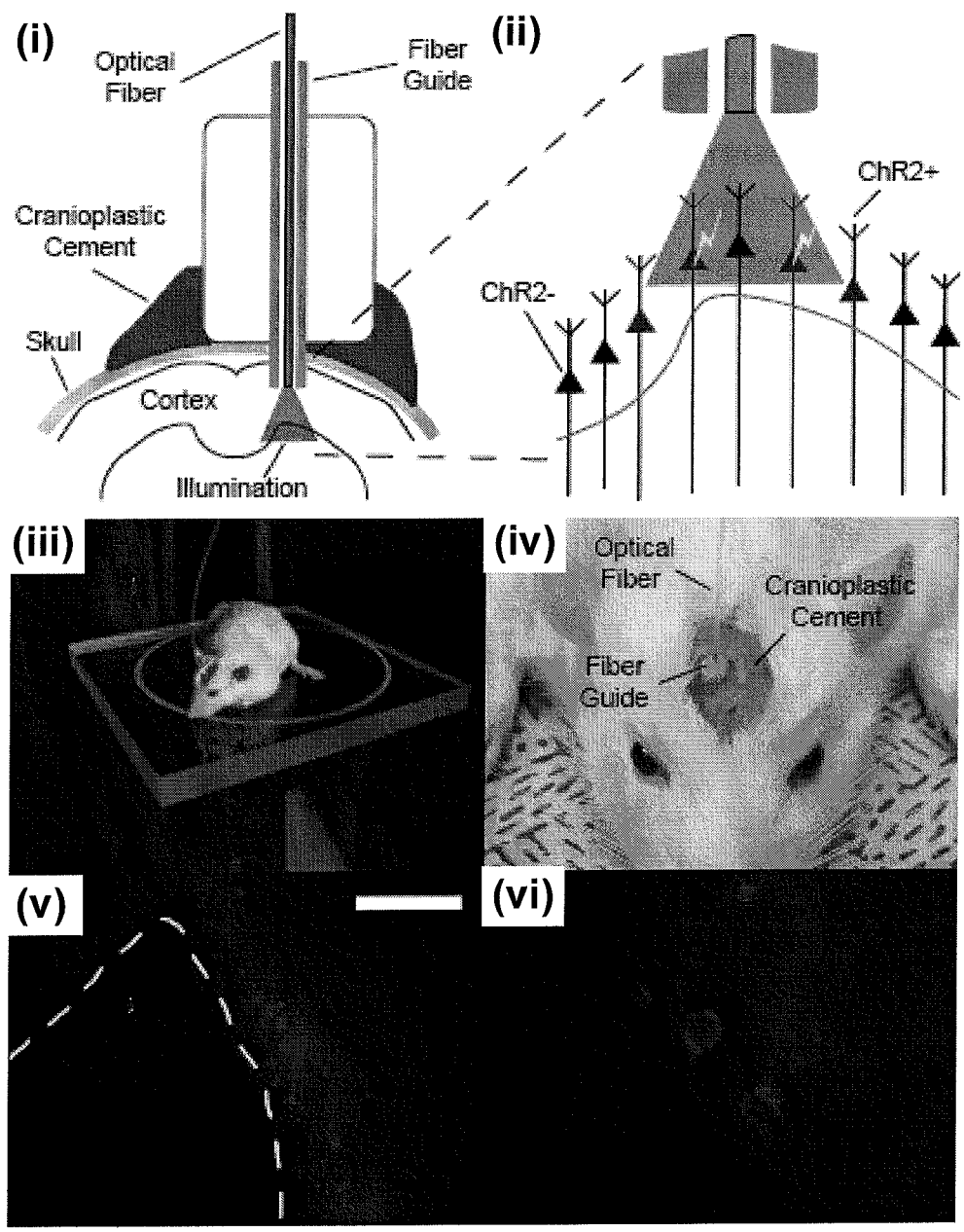

As applied to human skull and a rat skull, FIGS. 1A and 1B provide an overview of an optical neural interface, in accordance with the present invention. FIGS. 1A and 1B illustrate similar optical neural interfaces which are mounted on a mammalian skull, showing an optical fiber guide, optical fiber inserted in the guide, and blue light transmitted to the cortex. As discussed in more detail below, optical neural interfaces, have a wide variety of applications for studies and treatment of a wide variety of functions and disorders. These functions and disorders are typically associated with specific neurons or anatomic locations.

FIG. 1A illustrates examples of several example anatomic locations for interventions in accordance with the methods herein described. An MRI image or patient 100 is shown in cross-sectional plane 110. Brain 140 contains numerous regions to which the methods detailed herein describe. As representative examples, five such anatomical regions and associated applications are illustrated. Brain region 115 depicts Brodmann Area 25, a depression treatment target as described below. Brain region 120 is the genu of the anterior cingulate, and a target for drug addiction treatment as described below. Brain region 125 is the prefrontal cortex, and a target for conditions including depression, as described below. Brain region 130 is anterior cingulate and corresponds with Brodmann Area 24, which is a target for pain disorders, as well as OCD and depression as described below. Brain region 135 is posterior cingulate gyrus, and is one of the targets for Alzheimer's disease, as described below.

In the specific case of the rat (FIG. 1B), two weeks prior to testing, a lentivirus carrying the ChR2 gene is fused to mCherry under control of the CaMKIIα promoter as injected through the fiber guide. FIGS. 1B(i) and 1B(ii) show a schematic of the stimulated region with the optical fiber tip flush with the fiber guide and blue light illuminating the deeper layers of motor cortex. Only glutamatergic pyramidal neurons that are both in the cone of illumination and genetically ChR2+ will be activated to fire action potentials. FIG. 1B(iii) shows the rat with the optical neural interface implanted, and showing blue light transmitted to target neurons via the optical fiber. FIG. 1B(iv) is a close-up view of the optical neural interface showing fiber guide attached with translucent cranioplastic cement. Note that no scalp or bone is exposed. FIG. 1B(v) is a low-power mCherry fluorescence image of an acute brain slice showing the rat motor cortex after removal of the optical neural interface. The edge of the potential space created by the fiber guide is demarcated with a dashed line. Numerous mCherry+ neurons around the distal end of the fiber guide are present. The scale bar is 250 µm. FIG. 1B(vi) is a high-power image of mCherry+ neurons at the edge of the fiber guide potential space, showing membrane-localized fluorescence characteristic of ChR2–mCherry fusion protein expression.

Figure 2:
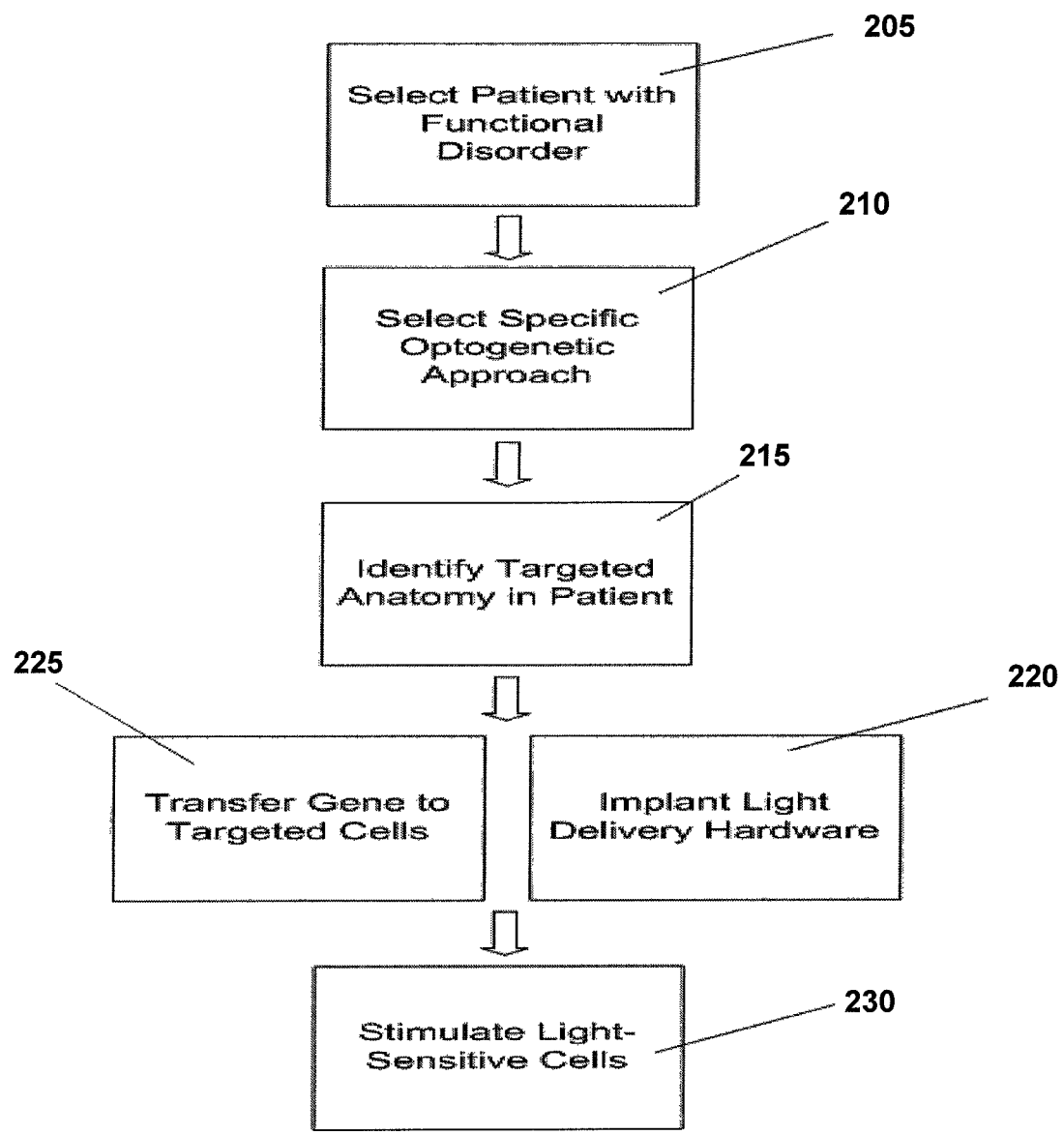
FIG. 2 is a flow chart showing one example of a method for optically targeting cells in a selected patient, according to the present invention.

As an example, FIG. 2 outlines a set of basic steps for one method that may be used in connection with the embodiments of the present invention. In step 205, the patient is selected or diagnosed as having a functional disorder of electrically-excitable cells, from a large number of possibilities, including those described herein. As part of this process, the neural circuitry, physiological feedback loops and associated mechanism of the disorder may be considered. In step 210, an applicable optogenetic approach is selected for the specific functional disorder. For example, in the case that the primary source of the problem is a hypoactive cell population, the selected approach might be an optogenetic excitation stimulation method to stimulate underactive cells, or the selected approach might be an optogenetic stabilization stimulation method to suppress another group of cells that serves to inhibit the underactive cells. In step 215 the targeted anatomy that corresponds with the known disease state and treatment strategy is identified within the actual patient. This may be done, for example, by direct visualization such as an open craniotomy or endoscope placement, or accomplished via functional imaging modalities such as functional magnetic resonance imaging (fMRI) and positron emission tomography (PET), and registered to the patient via surgical image guidance systems as are known in the art (for example, the StealthStation™ by Medtronic Navigation, of Louisville, Colo.). In step 220 a gene for light-sensitive ion channels or pumps, such as ChR2 or NpHR, is surgically applied to the appropriate anatomical location. As described in the above-referenced patent documents (by Karl Deisseroth et al.), for example, for use in the brain, injections of lentiviruses can be used to selectively express the Channelrhodopsin-2 (ChR2) protein in excitatory neurons. ChR2 is a genetically expressible, light-activated cation channel which has been previously developed for use in mammals, that can give rise to nontoxic, light-driven stimulation of CNS neurons on a timescale of milliseconds, allowing precise quantitative coupling between optical excitation and neuronal activation. The genetic specificity is achieved by using a transcription promoter that is specific to excitatory neurons (CamKIIα). Using this method ChR2 is expressed in excitatory neurons and not inhibitory neurons or glial cells.

In step 225, the light-pulsing hardware is surgically inserted and, optionally implanted. An example of such light pulsing hardware can include an optical fiber coupled to a light source such as a laser diode or LED (as in FIG. 1). The target cells are then illuminated via the fiber coupled light source. An example of such an optical neural interface (ONI) is used to activate ChR2 in an intact animal brain. The interface consists of an optical fiber guide stereotactically mounted to the skull with an optical fiber inserted through the guide. The fiber guide is composed of a cannula embedded in a mounting pedestal. For viral transduction of neurons, the fiber guide serves as an injection cannula to deliver the viral vector to the motor cortex. Then following expression of ChR2, the cannula is used to guide the optical fiber to the correct location, positioning the tip so the light beam is registered with the ChR2+ neurons. By using the same cannula for viral delivery and positioning of the optical fiber, the system ensures that the light beam is correctly registered to the ChR2+ neurons. A rat with the ONI implanted can have blue light transmitted to the ChR2+ neurons. The fiber guide can be attached with cranioplastic cement and an optical fiber inserted into the guide.

Steps 225 and 220 may be performed in either order, or in an integrated concurrent or simultaneous fashion, and are hence shown on the same vertical level of FIG. 2, in accordance with previously-disclosed methods (see e.g., Zhang, F., L. P. Wang, E. S. Boyden, and K. Deisseroth, "Channelrhodopsin-2 and optical control of excitable cells", Nat Methods, 2006. 3 (10): p. 785-92; and Aravanis, A. M. et al. An Optical Neural Interface In Vivo Control of Rodent Motor Cortex with Integrated Fiberoptic and Optogenetic Technology. Journal of Neural Engineering, 2007, as well as the above-mentioned patent documents. In step 230 the stimulation device is turned on, as also described in the above-mentioned documents.

Various implementations of the present invention would activate or affect difference volumes of tissue. Larger volumes of activation could be important in other settings, for example in large-scale neural prosthetic applications. However, measurements and calculations are believed to give rise to a lower limit on volume of tissue activatable with the ONI. Neurons at higher physiological temperatures are believed to be more excitable than those in in vitro experiments in which light power requirements were quantitatively measured. Moreover, while optical fiber can be made relatively thin (e.g., 1.27 mm), enlarging the fiber markedly enlarges the volume of tissue activated (e.g., 20 mm$^3$ for a 1 mm diameter optical fiber).

Figure 3:
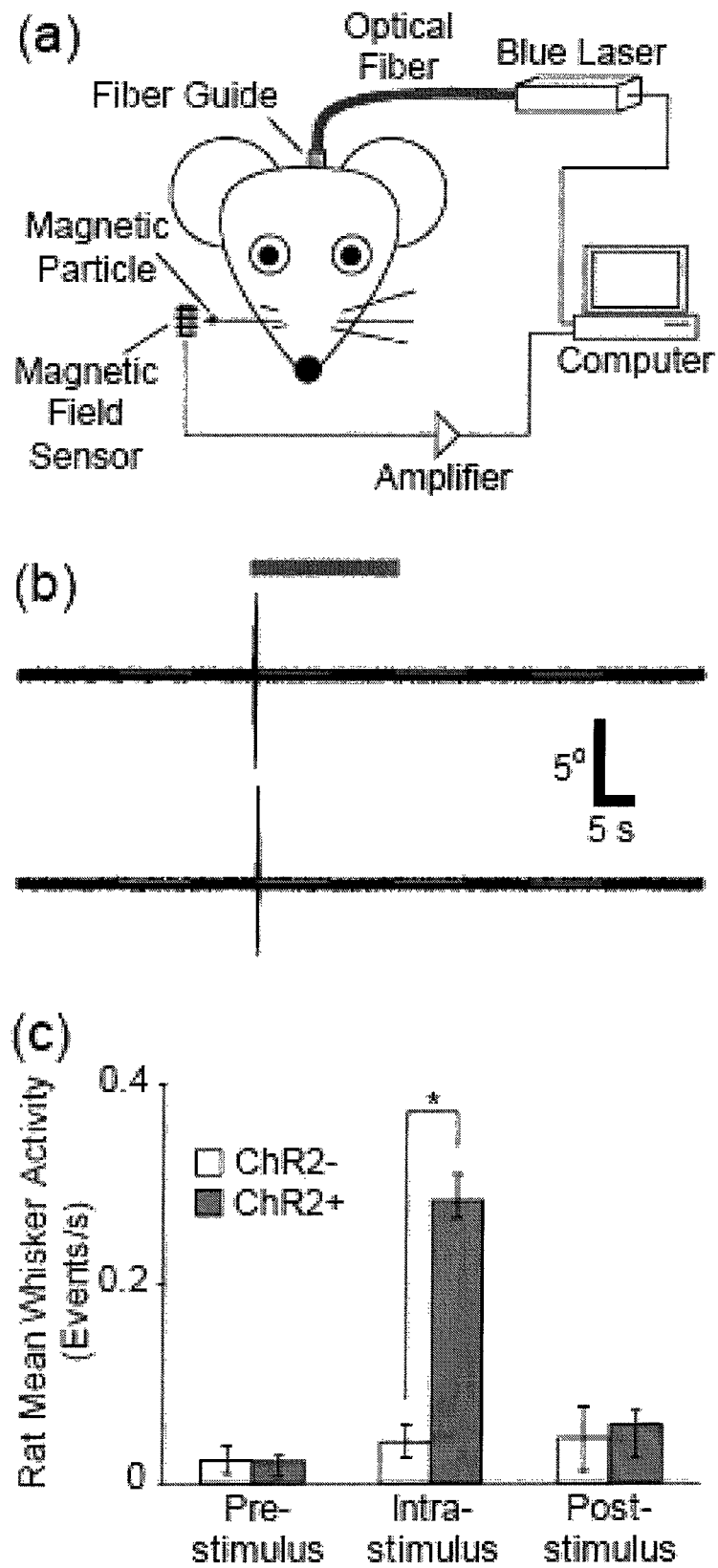
FIG. 3A shows a diagram of test setup involving mouse whisker deflection, consistent with an example embodiment of the present invention.
FIG. 3B shows detected whisker deflection relative to the stimulating light, consistent with an example embodiment of the present invention.
FIG. 3C shows detected whisker deflection with and without CHR2 and with and without stimulating light, consistent with an example embodiment of the present invention.

As an example demonstration of the effectiveness of the present invention as generally applicable to mammalian specimens, the present invention has been applied to control the respective motor functions of various species including, for example, rats and mice. Specifically, by applying the invention to a rat vibrissal motor cortex, whisker movements are evoked as shown in FIG. 3. Also in connection with the present invention, it has been discovered that pulsed blue light delivered via the optical neural interface repeatedly evokes whisker deflections in the rat of up to 10°. The mean number of whisker deflection events during stimulation is significantly higher in the ChR2+ rats than in the ChR2− control rats ($p<0.05$).

In accordance with the present invention, FIGS. 3a, 3b and 3c illustrate a specific optical neural interface as demonstrated to optically control the motor output of a rat. FIG. 3a is a schematic of a whisker movement measurement arrangement using optical neural interface to activate rat vibrissal motor cortex: the blue laser diode was coupled to a 200 μm multi-mode silica-core optical fiber. The fiber was directed at the motor cortex using the implanted fiber guide. Blue light (473 nm) was transmitted to the vibrissal motor cortex via the optical fiber. Whisker movements were measured magnetically; a magnetic particle was attached to the contralateral C2 vibrissa and a magnetoresistive sensor was placed near the particle. Changes in the voltage were amplified electronically and recorded to a computer. The signal was high-pass filtered at 10 Hz to remove low-frequency drift. FIG. 3b shows whisker activity in a ChR2+ rat in response to a 20 s continuous pulse of blue light. The scale bars are 5° and 5 s. FIG. 3c shows rat mean whisker activity pre-stimulus, intra-stimulus, and post-stimulus. The mean number of whisker twitching events was significantly greater in the ChR2+ rats (lentivirus injected through the fiber guide, n=2) than in the ChR2− rats (vehicle injected through fiber guide, n=2), *$p<0.05$.

Figure 4:
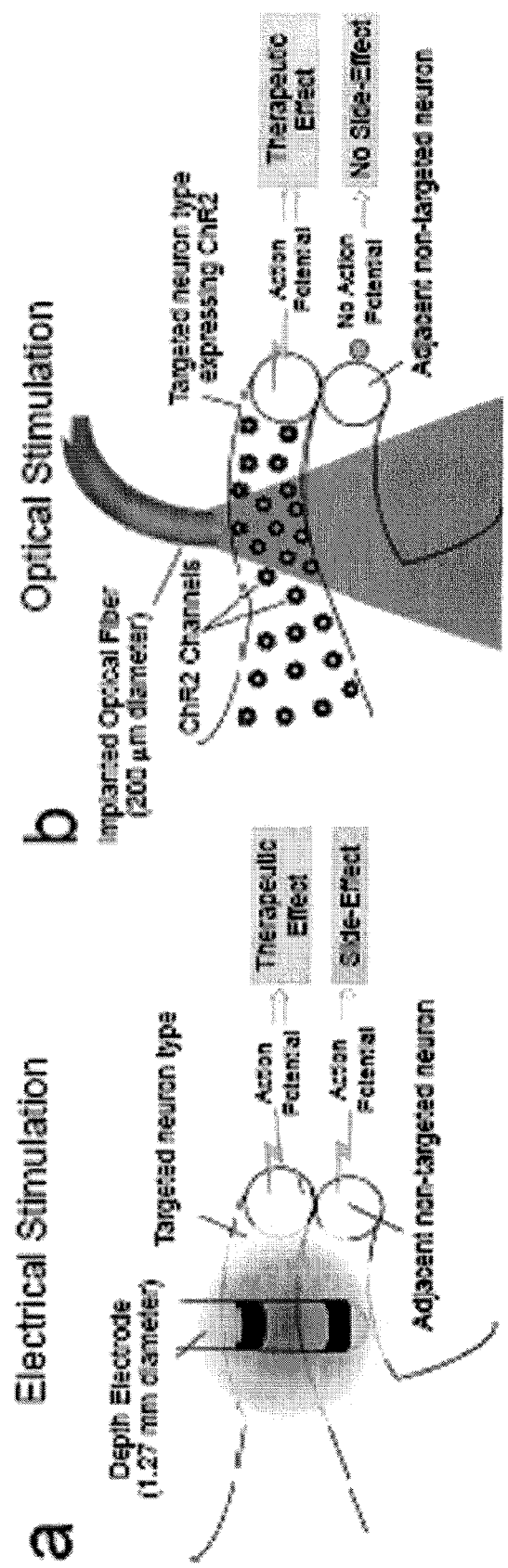
FIG. 4A shows electrode-based cell stimulation; consistent with an example embodiment of the present invention.
FIG. 4B illustrates optical stimulation of genetically-targeted cells, consistent with an example embodiment of the present invention.

Relative to electrode-based cell stimulation as illustrated in FIG. 4a, FIG. 4b illustrates optical stimulation of genetically-targeted cells. FIG. 4b shows ChR2 expression to a specific neuron population. In this example, ChR2 expression is specific to the excitatory CaMKIIα-expressing cortical neuron population. Thus, one embodiment of the optical neural interface is particularly useful for activating the specific target cells without affecting other cells (e.g., activating excitatory cortical neurons and not other cell types such as inhibitory neurons or glial cells). Embodiments of the present invention also allow for the use of both electrical and optical stimulation.

Figure 5:
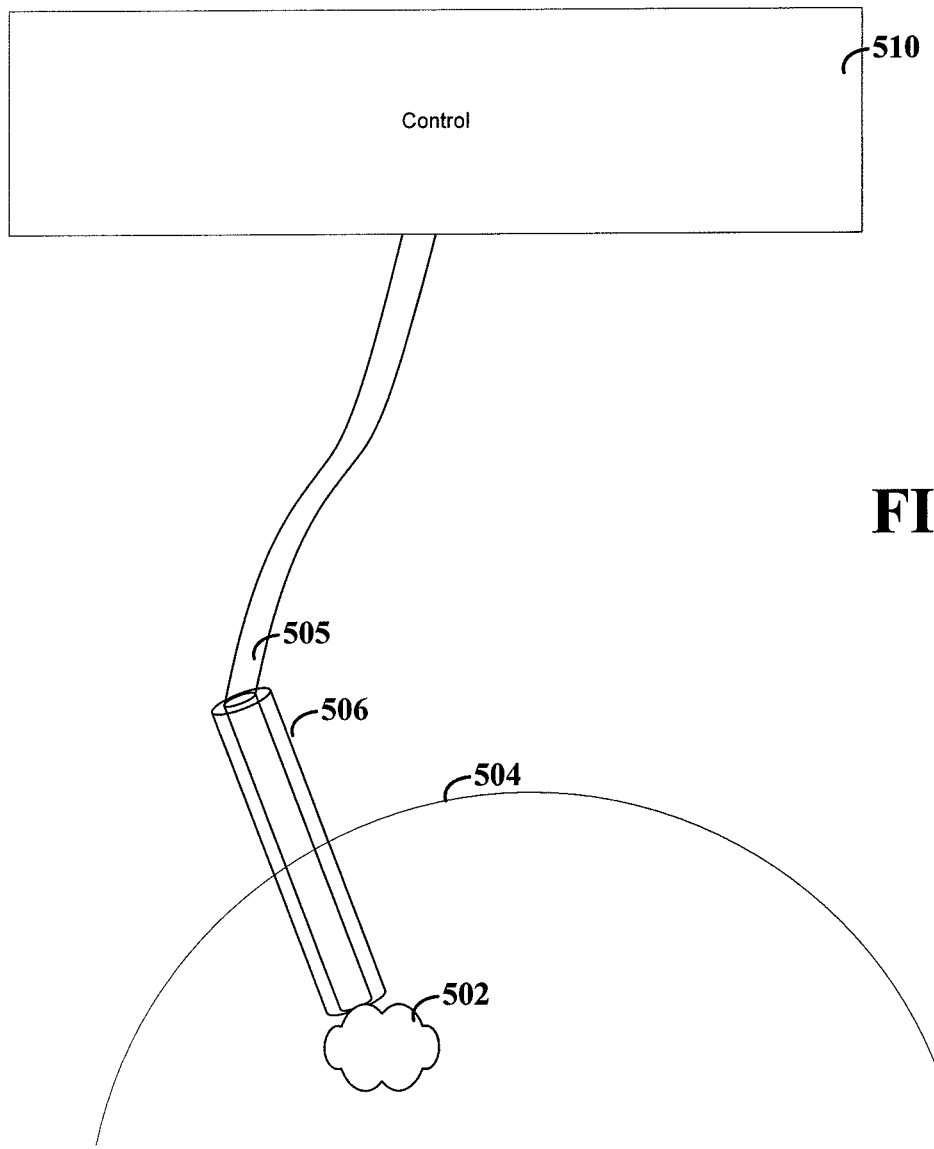
FIG. 5 shows an example of an optical neural interface used for neural stimulation of the brain, according to an example embodiment of the present invention.

FIG. 5 shows an example of an optical neural interface (ONI) device for optically stimulating target cells 502. Cannula 506 is inserted through the skull 504 of the patient. This can be done using a variety of surgical procedures, such as a sterotatic surgery. Once cannula 506 is properly positioned, genetic modifiers are introduced to target cells 502 through cannula 506. Subsequently, a light deliver mechanism 508 uses cannula 506 to deliver light to the target cells. In a specific example, light delivery mechanism 508 includes an optical fiber that is inserted through cannula 506. Another implementation uses a combination of mirrors and/or lens elements to direct light to the target cells.

Control 510 may modify the properties of the optical pulses (e.g., frequency, intensity and duration). In a particular embodiment, control 510 includes one or more lasers that generate light at a frequency that corresponds to the optical properties of the target cells. For instance, cells modified with ChR2 have been shown to respond to light corresponding to wavelengths around 400 to 900 nm, and more particularly, to wavelengths of about 470 nm. In addition to providing or controlling the wavelength of the light, the power and temporal characteristics of the light may also be controlled. By varying the intensity or power of the light, the strength of the reaction from the target cells 502 may be varied accordingly. Due to diffusion of the light within the tissue, the intensity of the light generally reduces as the distance from the light source increases. Thus, by increasing the intensity of the light the amount of tissue receiving enough light to activate the light responsive channels or pumps can be increased.

According to a specific embodiment of the present invention, the optical stimulus may be directed at specific target area(s) within the target tissue. In one instance, micro-Electro-Mechanical Systems (MEMS) or servo controlled oscillating mirrors can be used to direct the optical stimulus at a specific location or stimulus point. The stimulus point can be further focused using an objective lens. In a particular embodiment, a scanning microscopy technique, such as laser scanning confocal microscopy, is used to direct the light toward the desired stimulus point. In this manner, light may be scanned across the target cells. The effectiveness and/or results of stimulus at each location within the scan can be monitored and used to determine the most desirable treatment. In another instance, a specific target cell area may be targeted or certain portions of the target cells may be stimulated in a specific sequence.

According to another embodiment of the present invention, the cannula may be inserted near various nerves or muscles. In a particular example of such a use, the cannula may be inserted near various portions of the conduction system of the heart. As an example, the cannula may be inserted near the sinoatrial node (SA) of a patient who exhibits cardiac pacing abnormalities, such as tachycardia and bradycardia. The stimulus may then be used to increase the heart rate (for bradycardia), decrease the heart rate (for tachycardia) or otherwise control the heart rate. Pacing the heart using externally generated electrical pulses (e.g., from electrical contacts) may produce unwanted capture characteristics, such as long QRS waves, and may also suffer from increasing voltage thresholds due to anodal blocking. Optical stimulus may be particularly useful for generating a pseudo-intrinsic pulse (e.g., a pulse voltage that originates from an action potential rather than an electrical contact).

In various embodiments, the cannula may be implemented with at least a portion of the cannula that is flexible. For instance, the cannula may function as a catheter that can be inserted through veins or arteries and into the heart. A fixation device may be included to attach one end of the cannula near the target cells. For further details on catheter devices and their use in cardiac applications, reference may be made to U.S. Pat. No. 4,559,951 to Dahl et al. and entitled "Catheter Assembly," which is fully incorporated herein by reference.

Figure 6:
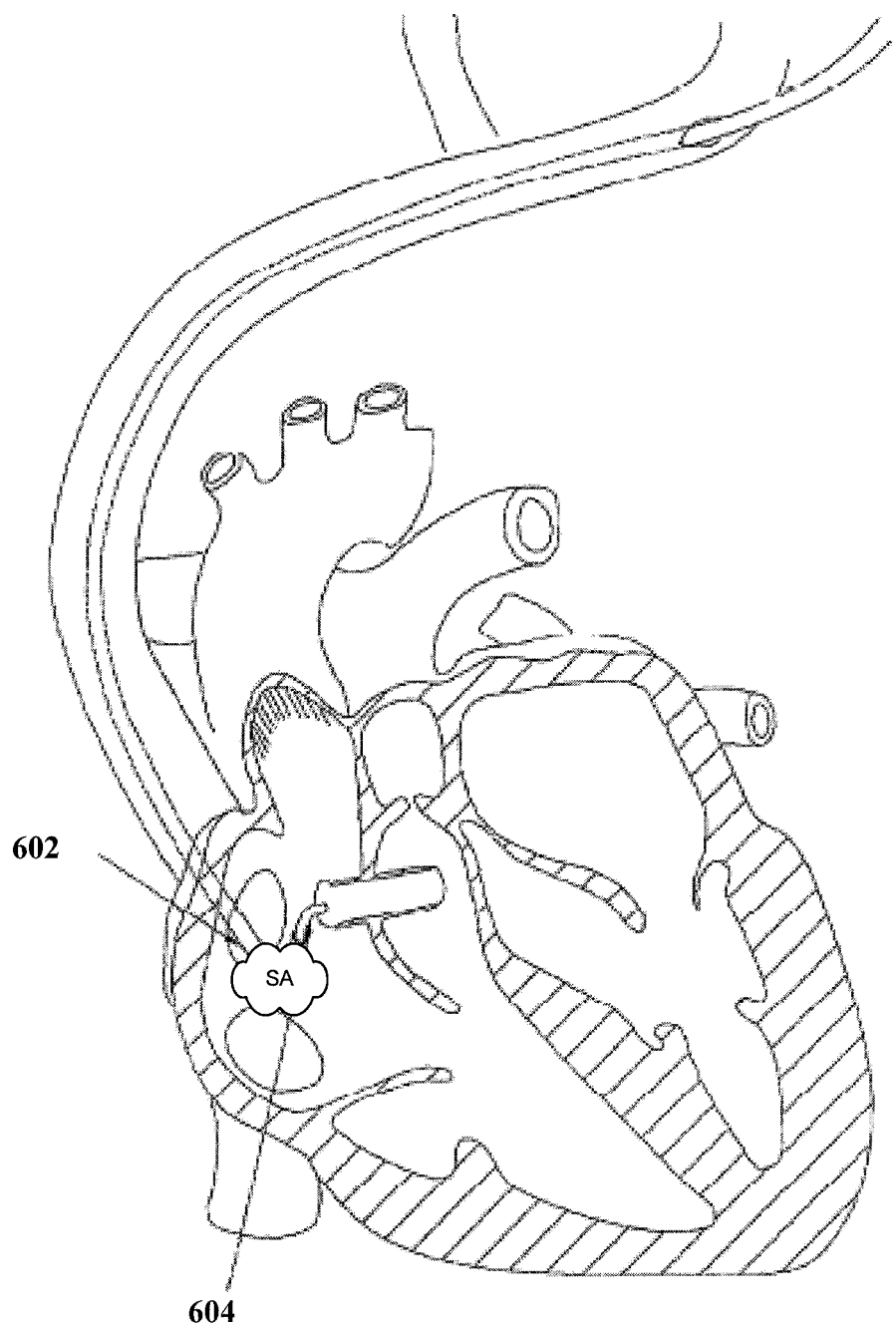
FIG. 6 shows an example of an optical neural interface used for endocardial stimulation of the heart; according to an example embodiment of the present invention.

FIG. 6 shows an example of an optical neural interface used for endocardial stimulation of the heart; according to an example embodiment of the present invention. The genetic modifiers are guided to the desired location using the cannula 602. The cannula 602 is guided into the heart through various techniques, such as those used in connection with the implantation of electrical pacing systems. For instance, the cannula can be fed through one of several veins or arteries into the desired atrium or ventricle of the heart. In a specific example, the cannula is fed into the right atrium to a location near the SA 604. The cannula maybe affixed to (or near) the SA using tines, a screw, barbs or other suitable attachment mechanisms. The genetic modifiers can then be delivered to the target neural cells within the SA. Fiber optics is then inserted through cannula 602 and optical stimulus may then be used to pace or otherwise control the heart.

Figure 7:
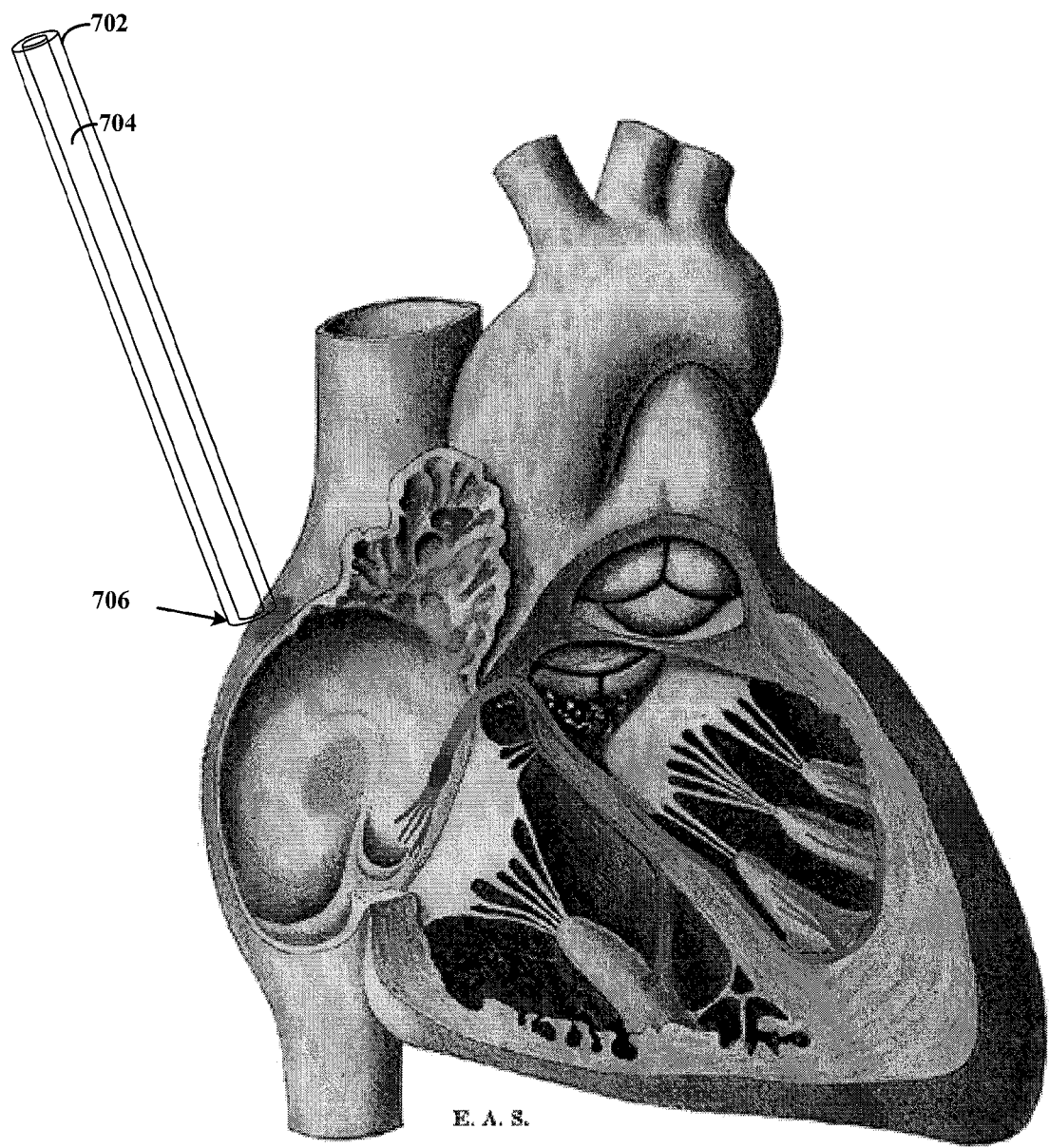
FIG. 7 shows an example of an optical neural interface used for epicardial stimulation of the heart; according to an example embodiment of the present invention.

FIG. 7 shows an example of an optical neural interface used for epicardial stimulation of the heart; according to an example embodiment of the present invention. The cannula 702 is surgically implanted near or into the epicardial (exterior wall) of the heart to allow for stimulus of the target cells 706. The genetic modifiers and optical stimulus are delivered via the inner lumen 704 of the cannula 702. In some instances, the use of optical stimulus in place of other stimulus methods, such as electrical stimulus via electrodes, may result in distinct stimulus characteristics. For instance, electrical conductivity of tissue often does not correspond to optical diffusion characteristics, electrical stimulus may be difficult to direct, and optical diffusion does not necessarily correspond to electrical fields and current flow.

While the invention is not so limited, various aspects of the invention may be better understood in the context of specific embodiments of the invention. According to one such embodiment, a solid-state laser diode that can be pulsed with millisecond precision and that outputs 20 mW of power at 473 nm is coupled to a lightweight, flexible multimode optical fiber that is about 200 μm in diameter. Specific targeting of ChR2 in excitatory cells in vivo may be accomplished using the CaMKIIα promoter. Under these conditions, the power density of light exiting the fiber (e.g., around 380 mW/mm) has been found to be sufficient for driving excitatory neurons in vivo and control motor cortex function in intact rodents. For animals with naturally occurring all-trans-retinal (ATR) in sufficient quantities, such as mammals, no exogenous chemical cofactor is needed.

The in vivo tissue may produce significant attenuation of the laser intensity. Notwithstanding, a power density of light exiting the fiber end at 380 mW/mm$^2$ is believed to be sufficient to excite ChR2+ neurons within millimeters of the fiber end.

A specific embodiment of the present invention may be explained in connection with the following methodology as conducted on mammalian subjects. Rats (male Wistars, 250-350 g) and mice (female C57/BL6, 25-30 g) were anaesthetized by i.p. injection (90 mg ketamine and 5 mg xylazine per kg of rat body weight). A concentrated lentivirus solution was stereotactically injected into the rat motor cortex (anteroposterior =−1.5 mm from bregma; lateral=1.5 mm; ventral=1.5 mm) using an ONI device. For electrophysiological experiments, 2 weeks post-injection, 250 μm cortical slices were prepared in ice-cold cutting buffer (64 mM NaCl, 25 mM NaHCO$_3$, 10 mM glucose, 120 mM sucrose, 2.5 mM KCl, 1.25 mM NaH$_2$PO$_4$, 0.5 mM CaCl$_2$ and 7 mM MgCl$_2$, equilibrated with 95% O$_2$/5% CO$_2$) using a vibratome (VT 1000 S; Leica). After a recovery period of 30 min in cutting buffer at 32-35° C., slices were gently removed to a recording chamber mounted on an upright microscope (DM LFSA, Leica) and continuously perfused at a rate of 3-5 ml/min with carbonated ACSF (124 mM NaCl, 3 mM KCl, 26 mM NaHCO$_3$, 1.25 mM NaH$_2$PO$_4$, 2.4 mM CaCl$_2$, 1.3 mM MgCl$_2$, 10 mM Glucose), ventilated with 95% O$_2$/5% CO$_2$.

Motor cortex slices were visualized by standard transmission optics on an upright fluorescence microscope (DM LFSA; Leica) with a 20×, 0.5 NA water immersion objective. mCherry expressing cells located about 10-30 μm below the surface of the slice were visualized with a TXRED filter set (TXRED 4040B, exciter 562 nm, dichroic 530-585 nm, emitter 624 nm; Semrock). Images were recorded with a cooled CCD camera (Retiga Exi; Qimaging). Electrophysiological recordings in neurons were performed. For instance, membrane currents were measured with the patch-clamp technique in the whole cell voltage-clamp configuration using Axon Multiclamp 700B (Axon Instruments) amplifiers. Pipette solution consisted of (in mM): 97 potassium gluconate, 38 KCl, 6 NaCl, 0.35 sodium ATP, 4 magnesium ATP, 0.35 EGTA, 7 phosphocreatine and 20 HEPES (pH 7.25 with KOH). Pipette resistance was 4-8 MΩ. To obtain an estimate of the resting potential, the membrane potential at the time of establishing the whole cell configuration was recorded. pClamp 9 software (Axon Instruments) was used to record all data. For ChR2 activation, blue light pulses were generated using the DG-4 high-speed optical switch with a 300 W xenon lamp (Sutter Instruments) and a GFP filter set (excitation filter HQ470/40X, dichroic Q495LP; Chroma). The light pulses were delivered to the slice through a 20× objective lens (NA 0.5; Leica) yielding a blue light power density of 10 mW/mm$^2$, measured with a power meter (1815-C; Newport). Electrophysiological experiments were performed at room temperature (22-24° C.).

Light transmission measurements were conducted with acute brain slices from a 300 g rat and a 30 g mouse. Brain slices of thicknesses between 200 μm and 1 mm were cut in 0-4° C. sucrose solution using a vibratome (Leica; VT1000S). The brain slices were then placed in a Petri dish containing the same sucrose solution over the photodetector of a power meter (ThorLabs; S130A). The tip of a 200 μm optical fiber (BFL37-200; Thorlabs) coupled to a blue diode laser (473 nm, Crystal Laser) was mounted on a micromanipulator and then positioned over the cortical tissue in the slice, normal to the slice and detector. The tip was submerged into the solution and moved to 1 mm above the tissue surface. Blue light from the diode laser was delivered to the tissue via the optical fiber and a measurement of the total light power was recorded from the power meter. The fiber tip was then translated horizontally, so that a blank measurement without tissue present could be taken. For each slice, 1 measurement was taken from each hemisphere. For each tissue thickness value, 2 different slices were cut and measured. Transmission fraction was calculated as the power with tissue present divided by the power with no tissue present. Transmission of light through the brain slices was modeled using the Kubelka-Munk model for diffuse scattering media, T=1/(Sx+1), where T is transmission fraction, S is the scatter coefficient per unit thickness, and x is the thickness of the sample. The model assumes that the sample is a planar, homogeneous, ideal diffuser, and illuminated on one side with diffuse monochromatic light. The model further assumes that reflection and absorption are constant over the thickness of the sample. To further simplify the model, it was also assumed that no absorption occurs. This assumption is based on previous in vivo and in vitro data showing that in mammalian brain tissue, transmission loss from scattering is much greater than loss from absorption for wavelengths ranging from 400 to 900 nm. Best fit values for S were 11.2 mm$_{-1}$ for mouse and 10.3 mm$_{-1}$ for rat. The relationship of power density to tissue penetration distance was estimated by taking the product of the measured transmission fraction (remaining light not scattered or absorbed) and the calculated fractional decrease in power density due to the conical geometry of emitted light at a given distance in the absence of tissue scattering and absorption. The geometric decrease in power density with distance from the fiber end x was calculated using the NA (0.37) of the optical fiber, I(x)/I(o)=y$^2$/((Sx+1)(x+y)$^2$), (geometric component only) where $$y = r\sqrt{\left(\frac{n}{NA}\right)^2 - 1},$$

r is the diameter of the optical fiber, and n is the index of refraction of grey matter (e.g., 1.36). The complete expression for power density taking into account both the scattering and geometric losses is $$\frac{I(x)}{I(o)} = \frac{y^2}{(Sx+1)(x+y)^2}.$$

Surgeries were performed under aseptic conditions. For anesthesia, ketamine (90 mg/kg of rat body weight; 16 mg/kg of mouse body weight) and xylazine (5 mg/kg of rat body weight; 5 mg/kg of mouse body weight) cocktail was injected i.p. The level of anesthesia was carefully monitored and maintenance doses of anesthesia were given as needed. Fur was sheared from the top of the animal's head and the head was placed in a stereotactic positioning rig. A midline scalp incision was made and a 1-mm-diameter craniotomy was drilled: (rat: anteroposterior=−1.5 mm from bregma, lateral=1.5 mm); (mouse: anteroposterior=−1 mm from bregma, lateral=1 mm). A fiber guide (C313G; Plastics1) was then inserted through the craniotomy to a depth of 1.5 mm in the rat and 1.3 mm in the mouse. Three skull screws (00-96X 3/32; Plastics1) were placed in the skull surrounding the fiber guide pedestal, and cranioplastic cement (Ortho-Jet; Lang Dental) was used to anchor the fiber guide system to the skull screws. After 30 minutes, the free edge of the scalp was brought to the base of the cranioplastic cement using sutures (3-0 silk; Ethicon) and tissue adhesive (Vetbond; 3M). A 2 µL aliquot of concentrated lentiviruses in solution (described above) was slowly injected through the fiber guide using an internal cannula (C313I; Plastics1) over 5 minutes. After waiting 10 more minutes for diffusion of the lentivirus, the internal cannula was withdrawn, and a dummy cannula (C313G; Plastics1) was inserted to keep the fiber guide open.

The animals were lightly anesthetized with a 50% dose of the ketamine and xylazine cocktail described above. For these experiments animals were kept in only a lightly sedated state, where whisker deflections spontaneously occurred, as heavier sedation abolished both spontaneous and evoked responses and with no sedation the spontaneous activity was so vigorous it obscured any evoked activity. Whiskers contralateral to the fiber guide implantation were trimmed to 1 cm in length, and a 1 mg rare-earth magnetic particle (neodymium-iron-boron; Magcraft) was attached to the C2 vibrissa. The head was then placed in a stereotactic rig with minimal pressure applied. To measure whisker movement, a magnetoresistive sensor (HMC1001; Honeywell) was mounted on a micromanipulator and moved near the magnetic particle. The signal was amplified (410; Brownlee) and recorded to a computer. Signals were high-pass filtered at 10 Hz to remove low-frequency drift arising from head movement and breathing. Stimulation of ChR2+ neurons was accomplished using a multimode optical fiber (NA 0.37) with a 200 µm silica core (BFL37-200; Thorlabs) coupled to a 473 nm diode pumped laser (20 mW output power uncoupled; Crystal Laser). The measured power density emanating from the fiber was 380 mW/mm². The distal end of the fiber was polished and the jacket was stripped; the fiber was inserted into the fiber guide and advanced until flush with the fiber guide end. The animal was then allowed to habituate to the setup. Experiments were initiated once spontaneous whisker twitches greater than 0.5° were present. During an experimental sweep, 30 s of pre-stimulus data, 20 s of intra-stimulus data (20 s pulse of blue light), and 30 s of post-stimulus data were recorded.

Three weeks after photo stimulation, a subset of mice were anesthetized with ketamine/xylazine and sacrificed by transcardial perfusion with ice cold 4% paraformaldehyde (PFA) in phosphate buffered saline (PBS). Extracted brains were incubated overnight in 4% PFA/PBS and for 48 hours in 30% sucrose/PBS. 40 µm sections were cut on a Leica freezing microtome and stored in cryoprotectant at 4° C. For immunostaining, free-floating sections were rinsed twice in Tris-buffered saline (TBS, pH 7.5) and blocked for 30 minutes in TBS++ (TBS/0.3% Triton X-100/3% Normal Donkey Serum [NDS]). Both primary and secondary antibody incubations were conducted overnight at 4° C. in TBS++ with NDS reduced to 1%; sections were washed repeatedly in TBS after each antibody incubation. Antibodies used were rabbit anti-dsRed (1:500, Clontech), mouse anti-CaMKIIα (1:200; Chemicon), mouse anti-GAD67 (1:500, Chemicon), Cy3 donkey anti-rabbit (1:1000; Jackson ImmunoResearch), and FITC donkey anti-mouse (1:1000, Jackson). Stained sections were mounted under PVA-Dabco (Sigma). Confocal images were acquired on a Leica TCS SP2 microscope.

One of skill in the art would recognize that these methods may be used and modified to be applicable for various animals and human uses. The optical neural interface (ONI) may be particularly useful in functionally activating ChR2 in an intact animal. One instance of the interface consisted of an optical fiber guide stereotactically mounted to the skull with an optical fiber inserted through the guide. The fiber guide is composed of a cannula embedded in a mounting pedestal. For viral transduction of neurons, the fiber guide can serve as an injection cannula to deliver the viral vector to the motor cortex. Then, following expression of ChR2, the cannula is used to guide the optical fiber to the correct location, positioning the tip so the light beam is registered with the ChR2+ neurons. By using the same cannula for viral delivery and positioning of the optical fiber, the light beam is correctly registered to the ChR2+ neurons.

Acute rat brain slices (2 weeks post-injection through the fiber guide with lentivirus carrying the ChR2-mCherry fusion protein) displayed large numbers of red-fluorescent layer 4, 5, and 6 neurons in motor cortex, revealing robust ChR2-mCherry expression. As expected, and required for the optical interface to function, the fluorescent neurons were located on the edge of the potential space created by the fiber guide. At higher magnification, the red fluorescence appeared to be preferentially localized to the plasma membrane in these neurons, consistent with previous observations of mCherry-ChR2 expression. This data suggested that the targeted expression and spatial registration functions of the cannula/fiber guide system could be suitable for implementing an optical neural interface.

Figure 8:
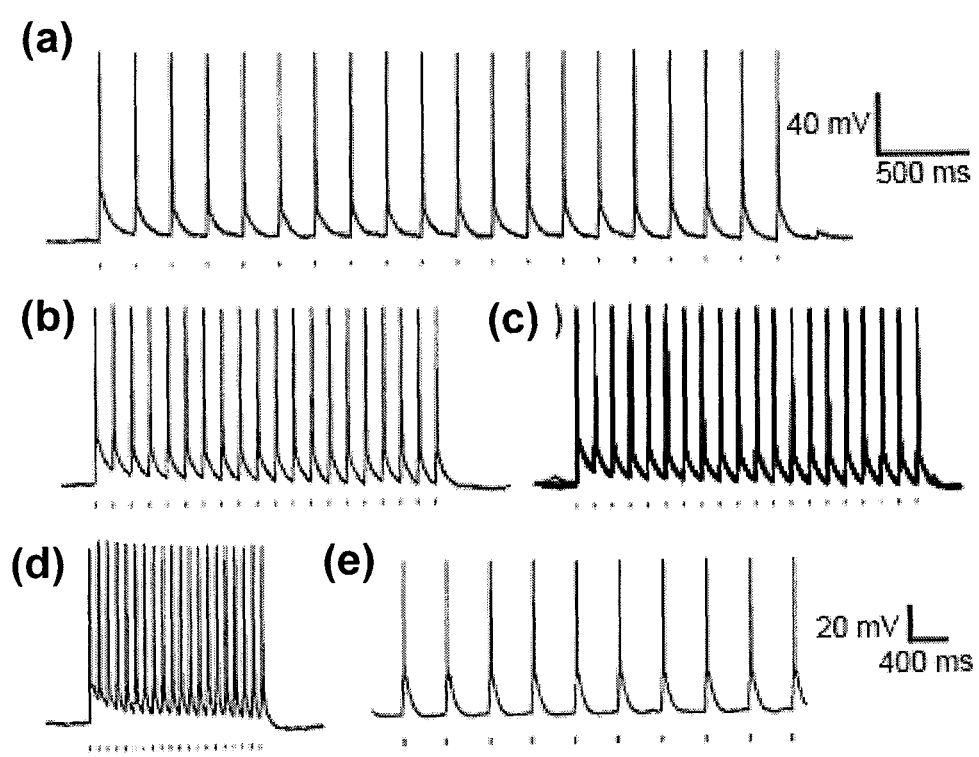
FIGS. 8a through 8e illustrate cell recordings that were obtained from a ChR2+ layer 5 motor neuron in acute brain slices that were prepared and processed according to the present invention.

To confirm that functional ChR2 could be expressed in the targeted excitatory motor neurons of layer 5 motor cortex, lentivirus carrying the ChR2-mCherry fusion protein under the control of an excitatory neuron-specific CaMKIIα promoter was stereotactically injected into rat vibrissal motor cortex, where brain slices of the injected region made 2 weeks post-injection showed the expected significant red fluorescence (mCherry) in the deeper layers of the cortex. In these same slices, it was next tested whether the level of ChR2 expression in these neurons and with this promoter would be sufficient to induce the depolarizing photocurrents required for action potential generation. Indeed, whole cell recordings obtained from these ChR2+ layer 5 motor neurons in acute brain slices showed robust spiking in response to illumination with blue light (473 nm; 10 mW/mm² generated by a 300 W xenon lamp and 20×, 0.5 NA objective) (FIG. 8a). In fact, the ChR2+ neurons were able to follow photostimulation trains (10 ms pulses) at 5, 10 and 20 Hz, as shown in FIGS. 8a, 8b and 8c. Moreover, the neurons generated an action potential for every light stimulus; FIG. 8d shows that failures were never observed even over multiple sustained trains of 10 Hz light pulses.

A fiber-coupled diode laser was evaluated for its ability to evoke photocurrent induced action potentials. Whole cell recordings were obtained from a ChR2+ layer 5 motor neuron in acute brain slices prepared as in FIG. 8a-e, illuminated in this case not by the xenon lamp and 20× objective, but by the polished end of a 200 μm multi-mode optical fiber. With the fiber tip placed 1 mm away from the microelectrode tip, the closest distance practically achievable, the neuron perfectly followed a train of photostimuli at 2 Hz (FIG. 8d). As the frequency increased beyond 2 Hz, there were an increasing number of failures, where the photocurrents evoked were insufficient to depolarize the neuron to the threshold of action potential generation. Since the light intensity exiting the fiber end is quite high (~380 mW/mm$^2$), the decrease in efficacy with fiber illumination at higher frequencies is likely due to a rapid decrease in the effective light intensity at significant distances distal to the fiber tip. Presumably, ChR2+ neurons close to the fiber received a higher light intensity and therefore followed action potential trains more reliably.

Figure 9:
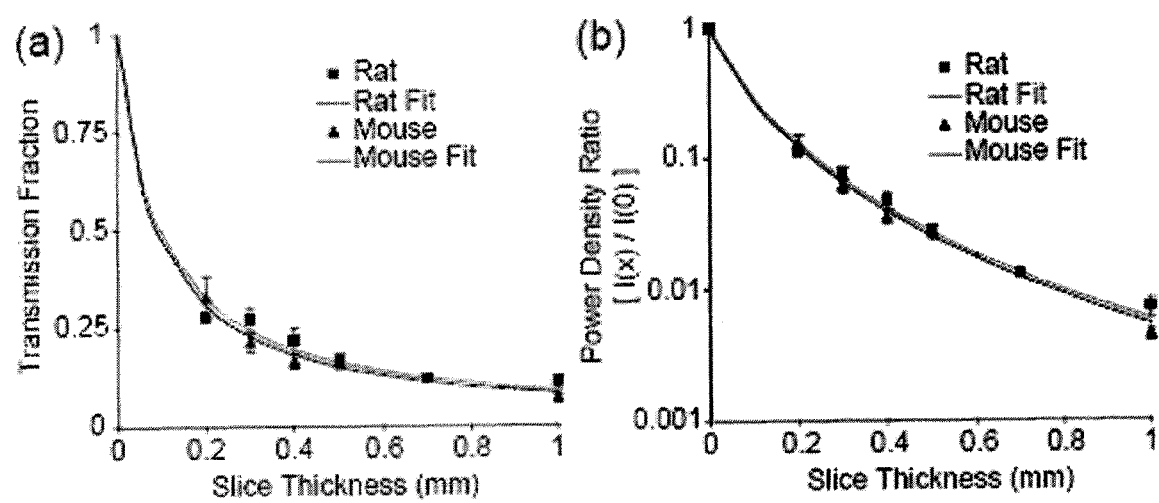
FIGS. 9A and 9B are graphs showing the effective light transmission/intensity for tissue penetration, as may be useful in connection with estimating expected tissue volume that is activated optical neural interfaces implemented and used in accordance with the present invention.

The following discussion addresses various physical processes and device parameters that may be used in determining the volume of ChR2+ neurons that can be effectively photostimulated. Such a volume should correspond to the brain volume in which the light intensity achieved is greater than 1 mW/mm$^2$, the minimum intensity required for generation of ChR2-evoked action potentials. The light intensity exiting the 200 μm diameter optical fiber tip is sufficiently intense to evoke action potentials (e.g., around 380 mW/mm$^2$). For these experiments, the blue light used for ChR2 activation (473 nm) is near the ChR2 peak absorption wavelength, but brain tissue highly scatters and weakly absorbs light at this wavelength. A direct measurement of the transmission fraction of total transmitted blue light as a function of distance through the rat and mouse cortical tissue was made. FIG. 9A shows that after passing through 100 μm of cortical tissue, total transmitted light power was reduced by 50%, and by 90% at 1 mm. Similar results were obtained in rat and mouse tissue, and both sets of data corresponded very well with the Kubelka-Munk model for diffuse scattering media, with best fit values for S of 11.2 mm$^{-1}$ for mouse and 10.3 mm$^{-1}$ for rat.

In addition to loss of light from scattering and absorption, light intensity also decreases as a result of the conical spreading of light after it exits the optical fiber. The light exiting the multimode fiber is not collimated and spreads with a conical angle of 32° determined by the numerical aperture of 0.37. This effect will reduce the power density of light, which may be a relevant quantitative parameter for determining efficacy of ChR2 stimulation. FIGS. 9A and 9B show the effective light density or intensity as calculated, taking into account the combined effects of scattering, absorption, and conical spread. The relationship of power density to tissue penetration distance was estimated by taking the product of the measured transmission fraction (total remaining light not scattered or absorbed) and the calculated fractional decrease in power density due to the conical geometry of emitted light at a given distance in the absence of tissue scattering and absorption. Using these experimental observations and calculations (e.g., FIG. 9B), the expected volume of tissue activated by this implementation of the optical neural interface was estimated. If effective ChR2-induced spiking is achieved at 1 mW/mm$^2$, then with the current laser diode and fiber optic technology the optical neural interface in principle will be capable of evoking spiking in neurons at least up to 1.4 mm from the fiber tip. This distance value, together with the measured conical cross-section of 1 mm diameter at 1.4 mm from the fiber tip, results in a total volume experiencing ≥1 mW/mm$^2$ light intensity of ~0.5 mm$^3$. This volume represents a substantial volume of brain tissue on the same order of magnitude as features on the somatotopic maps on motor cortex, and indicated to us that the optical design of the neural interface, in combination with the previously tested genetic design, could suffice to drive motor cortex function in the intact animal.

It was also tested whether the optical neural interface could be used to control motor output. Having demonstrated that functional ChR2 can be expressed in the deeper layers of vibrissal motor cortex, it was believed that activation of these neurons using the optical neural interface would cause detectable whisker movements. Previous work has shown that electrical stimulation of vibrissal motor cortex results in whisker deflections, and that firing of even a single layer 5 or 6 motor neuron will evoke deflections.

Figure 10:
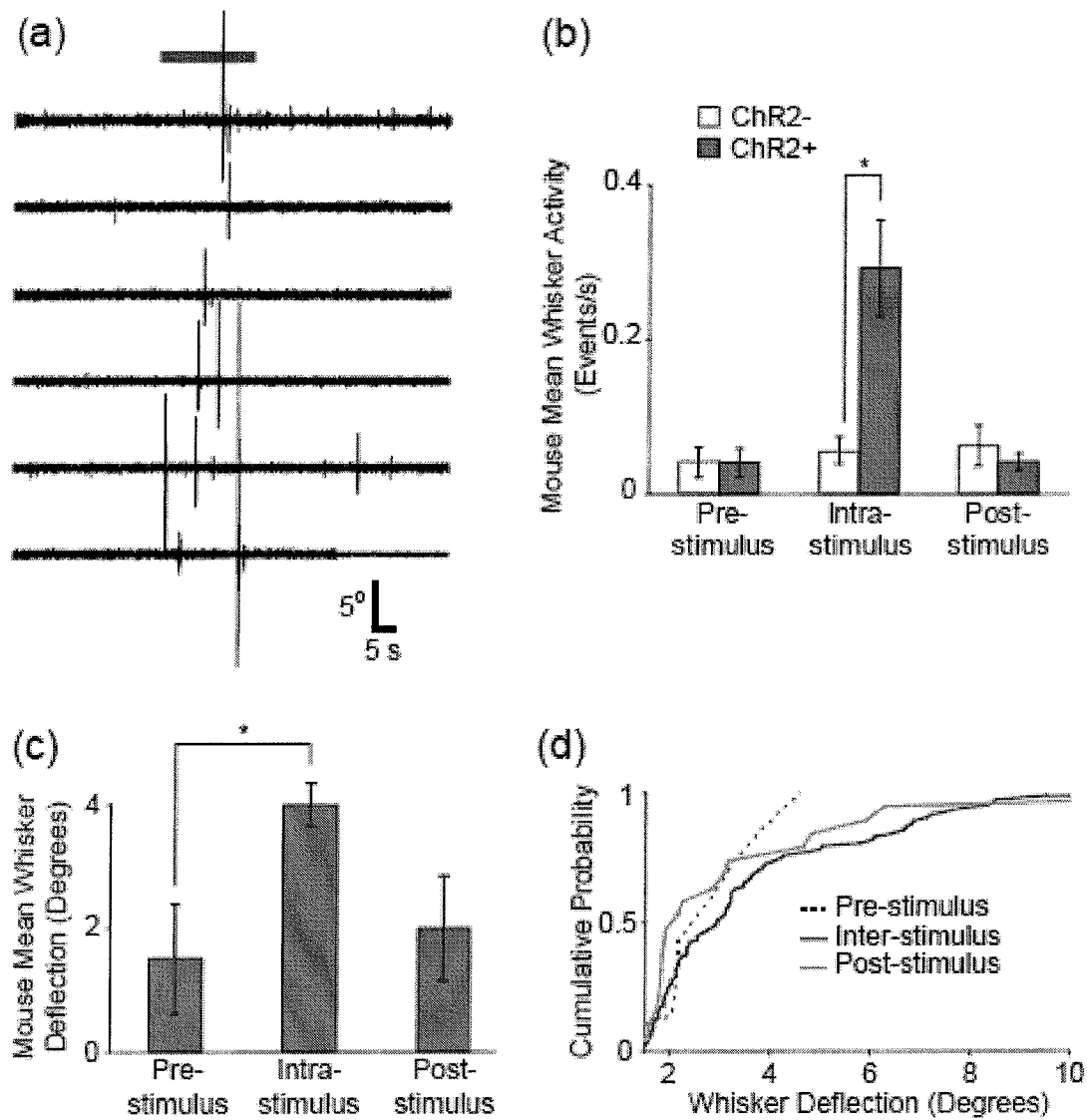
FIGS. 10A, 10B, 10C and 10D are diagrams showing the effectiveness of evoking whisker deflections as it relates to, optical neural interface implanted and tested in mice according to the present invention.

The laboratory rat is a widely used animal model for many neurological and psychiatric diseases relevant to brain stimulation work. However, mice are the ideal animal model for studying genetic contributions to nervous system physiology and pathology, despite the fact that mice can be more challenging for neural interface work due to their much smaller size. Therefore, the optical neural interfaces were also implanted and tested in mice. FIG. 10A shows that, as in the rat, 20-second blue light pulses delivered with the ONI evoked whisker deflections up to 20°. FIG. 10B shows that the mean number of deflections during the stimulus period was significantly higher in the ChR2+ mice than in the ChR2− mice ($p<0.05$). FIGS. 10C and 10D show that the amplitude of the whisker deflections demonstrated an increase during the stimulus period when compared with pre-stimulus period ($p<0.05$). Together, these data demonstrate successful implementation of an optical neural interface.

Confirmation of whether a select genetically defined set of neurons were in fact being stimulated via this integrated optical and genetic technology was obtained by employing immunohistochemistry to verify that ChR2 was expressed specifically in the excitatory cortical pyramidal neurons, as hypothesized from the use of the glutamatergic, neuron-specific, CaMKIIα promoter to drive ChR2 expression. Fixed brain sections of injected animals were immunostained as floating sections with an antibody for dsRed to label ChR2-mCherry, along with antibodies for either CaMKIIα or glutamate decarboxylase (GAD67), a GABA-producing enzyme that is specifically expressed in inhibitory interneurons. Representative confocal images of ChR2/CaMKIIα and ChR2/GAD67 immunostaining were taken for confirmation purposes. Nearly all of the ChR2-positive cells in the cortex also expressed CaMKIIα, and almost none expressed GAD67. Thus, ChR2 expression was specific to the excitatory CaMKIIα-expressing cortical neuron population. One embodiment of the optical neural interface may be particularly useful for activating the specific target cells without affecting other cells (e.g., activating excitatory cortical neurons and not other cell types such as inhibitory neurons or glial cells).

Many human applications of the present invention require FDA-approval prior to their use. For instance, human use of gene therapy may require such approval. However, similar gene therapies in neurons (nonproliferative cells that are non-susceptible to neoplasms) are proceeding rapidly, with active, FDA-approved clinical trials already underway involving viral gene delivery to human brains. This is likely to facilitate the use of various embodiments of the present invention for a large variety of applications. The following is a non-exhaustive list of a few examples of such applications and embodiments.

Addiction is associated with a variety of brain functions, including reward and expectation. Additionally, the driving cause of addiction may vary between individuals. According to one embodiment, addiction, for example nicotine addiction, may be treated with optogenetic stabilization of small areas on the insula. Optionally, functional brain imaging—for example cued-state PET or fMRI—may be used to locate a hypermetabolic focus in order to determine a precise target spot for the intervention on the insula surface.

Optogenetic excitation of the nucleus accumbens and septum may provide reward and pleasure to a patient without need for resorting to use of substances, and hence may hold a key to addiction treatment. Conversely, optogenetic stabilization of the nucleus accumbens and septum may be used to decrease drug craving in the context of addiction. In an alternative embodiment, optogenetic stabilization of hypermetabolic activity observed at the genu of the anterior cingulate (BA32) can be used to decrease drug craving. Optogenetic stabilization of cells within the arcuate nucleus of the medial hypothalamus which contain peptide products of pro-opiomelanocortin (POMC) and cocaine-and-amphetamine-regulating transcript (CART) can also be used to decrease drug addiction behavior. For further information in this regard, reference may be made to: Naqvi N H, Rudrauf D, Damasio H, Bechara A. Damage to the insula disrupts addiction to cigarette smoking. Science. 2007 Jan. 26; 315 (5811): 531-534, which is fully incorporated herein by reference.

Optogenetic stimulation of neuroendocrine neurons of the hypothalamic periventricular nucleus that secrete somatostatin can be used to inhibit secretion of growth hormone from the anterior pituitary, for example in acromegaly. Optogenetic stabilization of neuroendocrine neurons that secrete somatostatin or growth hormone can be used to increase growth and physical development. Among the changes that accompany "normal" aging, is a sharp decline in serum growth hormone levels after the $4^{th}$ and $5^{th}$ decades. Consequently, physical deterioration associated with aging may be lessened through optogenetic stabilization of the periventricular nucleus.

Optogenetic stabilization of the ventromedial nucleus of the hypothalamus, particularly the pro-opiomelanocortin (POMC) and cocaine-and-amphetamine-regulating transcript (CART) of the arcuate nucleus, can be used to increase appetite, and thereby treat anorexia nervosa. Alternatively, optogenetic stimulation of the lateral nuclei of the hypothalamus can be used to increase appetite and eating behaviors.

Optogenetic excitation in the cholinergic cells of affected areas including the temporal lobe, the NBM (Nucleus basalis of Meynert) and the posterior cingulate gyrus (BA 31) provides stimulation, and hence neurotrophic drive to deteriorating areas. Because the affected areas are widespread within the brain, an analogous treatment with implanted electrodes may be less feasible than an opto-genetic approach.

Anxiety disorders are typically associated with increased activity in the left temporal and frontal cortex and amygdala, which trends toward normal as anxiety resolves. Accordingly, the affected left temporal and frontal regions and amygdala may be treated with optogenetic stabilization, so as to dampen activity in these regions.

In normal physiology, photosensitive neural cells of the retina, which depolarize in response to the light that they receive, create a visual map of the received light pattern. Optogenetic ion channels can be used to mimic this process in many parts of the body, and the eyes are no exception. In the case of visual impairment or blindness due to damaged retina, a functionally new retina can be grown, which uses natural ambient light rather than flashing light patterns from an implanted device. The artificial retina grown may be placed in the location of the original retina (where it can take advantage of the optic nerve serving as a conduit back to the visual cortex). Alternatively, the artificial retina may be placed in another location, such as the forehead, provided that a conduit for the depolarization signals are transmitted to cortical tissue capable of deciphering the encoded information from the optogenetic sensor matrix. Cortical blindness could also be treated by simulating visual pathways downstream of the visual cortex. The stimulation would be based on visual data produced up stream of the visual cortex or by an artificial light sensor.

Treatment of tachycardia may be accomplished with optogenetic stimulation to parasympathetic nervous system fibers including CN X or Vagus Nerve. This causes a decrease in the SA node rate, thereby decreasing the heart rate and force of contraction. Similarly, optogenetic stabilization of sympathetic nervous system fibers within spinal nerves T1 through T4, serves to slow the heart. For the treatment of pathological bradycardia, optogenetic stabilization of the Vagus nerve, or optogenetic stimulation of sympathetic fibers in T1 through T4 will serve to increase heart rate. Cardiac dysrhythmias resulting from aberrant electrical foci that outpace the sinoatrial node may be suppressed by treating the aberrant electrical focus with moderate optogenetic stabilization. This decreases the intrinsic rate of firing within the treated tissue, and permits the sinoatrial node to regain its role in pacing the heart's electrical system. In a similar way, any type of cardiac arrhythmia could be treated. Degeneration of cardiac tissue that occurs in cardiomyopathy or congestive heart failure could also be treated using this invention; the remaining tissue could be excited using various embodiments of the invention.

Optogenetic excitation stimulation of brain regions including the frontal lobe, parietal lobes and hippocampi, may increase processing speed, improve memory, and stimulate growth and interconnection of neurons, including spurring development of neural progenitor cells. As an example, one such application of the present invention is directed to optogenetic excitation stimulation of targeted neurons in the thalamus for the purpose of bringing a patient out of a near-vegetative (barely-conscious) state. Consistent with the flow chart of FIG. 2 and other embodiments discussed herein, an elongated delivery structure is inserted into a narrow passageway of the patient's skull for inducing growth of light-gated ion channels or pumps in the membrane of targeted thalamus neurons. These modified neurons are then stimulated, e.g., via optics which may also gain access by the same passageway, by directing a flash of light thereupon so as to modulate the function of the targeted neurons and/or surrounding cells. For further information regarding appropriate modulation techniques (via electrode-based treatment) or further information regarding the associated brain regions for such patients, reference may be made to: Schiff N D, Giacino J T, Kalmar K, Victor J D, Baker K, Gerber M, Fritz B, Eisenberg B, O'Connor J O, Kobylarz E J, Farris S, Machado A, McCagg C, Plum F, Fins J J, Rezai A R. Behavioral improvements with thalamic stimulation after severe traumatic brain injury. Nature. Vol 448. Aug. 2, 2007 pp 600-604.

In an alternative embodiment, optogenetic excitation may be used to treat weakened cardiac muscle in conditions such as congestive heart failure. Electrical assistance to failing heart muscle of CHF is generally not practical, due to the thin-stretched, fragile state of the cardiac wall, and the difficulty in providing an evenly distributed electrical coupling between an electrodes and muscle. For this reason, preferred methods to date for increasing cardiac contractility have involved either pharmacological methods such as Beta agonists, and mechanical approaches such as ventricular assist devices. In this embodiment of the present invention, optogenetic excitation is delivered to weakened heart muscle via light emitting elements on the inner surface of a jacket surround the heart or otherwise against the affected heart wall. Light may be diffused by means well known in the art, to smoothly cover large areas of muscle, prompting contraction with each light pulse.

Optogenetic stabilization in the subgenual portion of the cingulate gyrus (Cg25), yellow light may be applied with an implanted device. The goal would be to treat depression by suppressing target activity in manner analogous to what is taught by Mayberg H S et al., Deep Brain Stimulation for Treatment-Resistant Depression. Neuron, Vol. 45, 651-660, Mar. 3, 2005, 651-660, which is fully incorporated herein by reference. In an alternative embodiment, an optogenetic excitation stimulation method is to increase activity in that region in a manner analogous to what is taught by Schlaepfer et al., Deep Brain stimulation to Reward Circuitry Alleviates Anhedonia in Refractory Major Depression, Neuropsychopharmacology 2007 1-10, which is fully incorporated herein by reference. In yet another embodiment the left dorsolateral prefrontal cortex (LDPFC) is targeted with an optogenetic excitation stimulation method. Pacing the LDLPFC at 5-20 Hz serves to increase the basal metabolic level of this structure which, via connecting circuitry, serves to decrease activity in Cg 25, improving depression in the process. Suppression of the right dorsolateral prefrontal cortex (RDLPFC) is also an effective depression treatment strategy. This may be accomplished by optogenetic stabilization on the RDLPFC, or suppression may also be accomplished by using optogenetic excitation stimulation, and pulsing at a slow rate—1 Hz or less, improving depression in the process. Vagus nerve stimulation (VNS) may be improved using an optogenetic approach. Use of optogenetic excitation may be used in order to stimulate only the vagus afferents to the brain, such as the nodose ganglion and the jugular ganglion. Efferents from the brain would not receive stimulation by this approach, thus eliminating some of the side-effects of VNS including discomfort in the throat, a cough, difficulty swallowing and a hoarse voice. In an alternative embodiment, the hippocampus may be optogenetically excited, leading to increased dendritic and axonal sprouting, and overall growth of the hippocampus. Other brain regions implicated in depression that could be treated using this invention include the amygdala, accumbens, orbitofrontal and orbitomedial cortex, hippocampus, olfactory cortex, and dopaminergic, serotonergic, and noradrenergic projections. Optogenetic approaches could be used to control spread of activity through structures like the hippocampus to control depressive symptoms.

So long as there are viable alpha and beta cell populations in the pancreatic islets of Langerhans, the islets can be targeted for the treatment of diabetes. For example, when serum glucose is high (as determined manually or by closed loop glucose detection system), optogenetic excitation may be used to cause insulin release from the beta cells of the islets of Langerhans in the pancreas, while optogenetic stabilization is used to prevent glucagon release from the alpha cells of the islets of Langerhans in the pancreas. Conversely, when blood sugars are too low (as determined manually or by closed loop glucose detection system), optogenetic stabilization may be used to stop beta cell secretion of insulin, and optogenetic excitation may be used to increase alpha-cell secretion of glucagon.

For treatment of epilepsy, quenching or blocking epileptogenic activity is amenable to optogenetic approaches. Most epilepsy patients have a stereotyped pattern of activity spread resulting from an epileptogenic focus Optogenetic stabilization could be used to suppress the abnormal activity before it spreads or truncated it early in its course. Alternatively, activiation of excitatory tissue via optogenetic excitation stimulation could be delivered in a series of deliberately ansynchronous patterns to disrupt the emerging seizure activity. Another alternative involves the activation of optogenetic excitation stimulation in GABAergic neurons to provide a similar result. Thalamic relays may be targeted with optogenetic stabilization triggered when an abnormal EEG pattern is detected.

Another embodiment involves the treatment of gastrointestinal disorders. The digestive system has its own, semi-autonomous nervous system containing sensory neurons, motor neurons and interneurons. These neurons control movement of the GI tract, as well as trigger specific cells in the gut to release acid, digestive enzymes, and hormones including gastrin, cholecystokinin and secretin. Syndromes that include inadequate secretion of any of these cellular products may be treated with optogenetic stimulation of the producing cell types, or neurons that prompt their activity. Conversely, optogenetic stabilization may be used to treat syndromes in which excessive endocrine and exocrine products are being created. Disorders of lowered intestinal motility, ranging from constipation (particularly in patients with spinal cord injury) to megacolan may be treated with optogenetic excitation of motor neurons in the intestines. Disorders of intestinal hypermotility, including some forms of irritable bowel syndrome may be treated with optogenetic stabilization of neurons that control motility. Neurogentic gastric outlet obstructions may be treated with optogenetic stabilization of neurons and musculature in the pyloris. An alternative approach to hypomobility syndromes would be to provide optogenetic excitation to stretch-sensitive neurons in the walls of the gut, increasing the signal that the gut is full and in need of emptying.

In this same paradigm, an approach to hypermobility syndromes of the gut would be to provide optogenetic stabilization to stretch receptor neurons in the lower GI, thus providing a "false cue" that the gut was empty, and not in need of emptying. In the case of frank fecal incontinence, gaining improved control of the internal and external sphincters may be preferred to slowing the motility of the entire tract. During periods of time during which a patient needs to hold feces in, optogenetic excitation of the internal anal sphincter will provide for retention. Providing optogenetic stimulation to the external sphincter may be used to provide additional continence. When the patient is required to defecate, the internal anal sphincter, and then external anal sphincter should be relaxed, either by pausing the optogenetic stimulation, or by adding optogenetic stabilization.

Conductive hearing loss may be treated by the use of optical cochlear implants. Once the cochlea has been prepared for optogenetic stimulation, a cochlear implant that flashes light may be used. Sensorineural hearing loss may be treated through optical stimulation of downstream targets in the auditory pathway.

Another embodiment of the present invention is directed toward the treatment of blood pressure disorders, such as hypertension. Baroreceptors and chemoreceptors in regions such as the aorta (aortic bodies and paraaortic bodies) and the carotid arteries ("carotic bodies") participate the regulation of blood pressure and respiration by sending afferents via the vagus nerve (CN X), and other pathways to the medulla and pons, particularly the solitary tract and nucleus. Optogentetic excitation of the carotid bodies, aortic bodies, paraortic bodies, may be used to send a false message of "hypertension" to the solitary nucleus and tract, causing it to report that blood pressure should be decreased. Optogenetic excitation or stabilization directly to appropriate parts of the brainstem may also be used to lower blood pressure. The opposite modality causes the optogenetic approach to serve as a pressor, raising blood pressure. A similar effect may also be achieved via optogenetic excitation of the Vagus nerve, or by optogenetic stabilization of sympathetic fibers within spinal nerves T1-T4. In an alternative embodiment, hypertension may be treated with optogenetic stabilization of the heart, resulting in decreased cardiac output and lowered blood pressure. According to another embodiment, optogentic stabilization of aldosterone-producing cells within the adrenal cortex may be used to decrease blood pressure. In yet another alternative embodiment, hypertension may be treated by optogenetic stabilization of vascular smooth muscle. Activating light may be passed transcutaneously to the peripheral vascular bed.

Another example embodiment is directed toward the treatment of hypothalamic-pituitary-adrenal axis disorders. In the treatment of hypothyroidism, optogenetic excitation of parvocellular neuroendocrine, neurons in the paraventricular and anterior hypothalamic nuclei can be used to increase secretion of thyrotropin-releasing hormone (TRH). TRH, in turn, stimulates anterior pituitary to secrete TSH. Conversely, hyperthyroidism may be treated with optogenetic stabilization of the provocellular neuroendocrine neurons. For the treatment of adrenal insufficiency, or of Addison's disease, optogenetic excitation of parvocellular neuroendocrine neurons in the supraoptic nucleus and paraventricular nuclei may be used to increase the secretion of vasopressin, which, with the help of corticotropin-releasing hormone (CRH), stimulate anterior pituitary to secrete ACTH. Cushing syndrome, frequently caused by excessive ACTH secretion, may be treated with optogenetic stabilization of the parvocellular neuroendocrine neurons of supraoptic nucleus via the same physiological chain of effects described above. Neuroendocrine neurons of the arcuate nucleus produce dopamine, which inhibits secretion of prolactin from the anterior pituitary. Hyperprolactinemia can therefore be treated via optogenetic excitation, while hypoprolactinemia can be treated with optogenetic stabilization of the neuroendocrine cells of the arcuate nucleus.

In the treatment of hyperautonomic states, for example anxiety disorders, optogenetic stabilization of the adrenal medulla may be used to reduce norepinephrine output. Similarly, optogenetic stimulation of the adrenal medulla may be used in persons with need for adrenaline surges, for example those with severe asthma, or disorders that manifest as chronic sleepiness.

Optogenetic stimulation of the adrenal cortex will cause release of chemicals including cortisol, testosterone, and aldosterone. Unlike the adrenal medualla, the adrenal cortex receives its instructions from neuroendocrine hormones secreted from the pituitary and hypothalamus, the lungs, and the kidneys. Regardless, the adrenal cortex is amenable to optogenetic stimulation. Optogenetic stimulation of the cortisol-producing cells of the adrenal cortex may be used to treat Addison's disease. Optogenetic stabilization of cortisol-producing cells of the adrenal cortex may be used to treat Cushing's disease. Optogenetic stimulation of testosterone-producing cells may be used to treat disorders of sexual interest in women: Optogenetic stabilization of those same cells may be used to decrease facial hair in women. Optogenetic stabilization of aldosterone-producing cells within the adrenal cortex may be used to decrease blood pressure. Optogenetic excitation of aldosterone-producing cells within the adrenal cortex may be used to increase blood pressure.

Optogenetic excitation stimulation of specific affected brain regions may be used to increase processing speed, and stimulate growth and interconnection of neurons, including spurring the maturation of neural progenitor cells as in Deisseroth et al., 2004. Such uses can be particularly useful for treatment of mental retardation.

According to another embodiment of the present invention, various muscle diseases and injuries can be treated. Palsies related to muscle damage, peripheral nerve damage and to dystrophic diseases can be treated with optogenetic excitation to cause contraction, and optogenetic stabilization to cause relaxation. This latter relaxation via optogenetic stabilization approach can also be used to prevent muscle wasting, maintain tone, and permit coordinated movement as opposing muscle groups are contracted. Likewise, frank spasticity can be treated via optogenetic stabilization.

In areas as diverse as peripheral nerve truncation, stroke, traumatic brain injury and spinal cord injury, there is a need to foster the growth of new neurons, and assist with their integration into a functional network with other neurons and with their target tissue. Re-growth of new neuronal tracts may be encouraged via optogenetic excitation, which serves to signal stem cells to sprout axons and dendrites, and to integrate themselves with the network. Use of an optogenetic technique (as opposed to electrodes) prevents receipt of signals by intact tissue, and serves to ensure that new target tissue grows by virtue of a communication set up with the developing neurons, and not with an artificial signal like current emanating from an electrode.

Obesity can be treated with optogenetic excitation to the ventromedial nucleus of the hypothalamus, particularly the pro-opiomelanocortin (POMC) and cocaine-and-amphetamine-regulating transcript (CART) of the arcuate nucleus. In an alternative embodiment, obesity can be treated via optogenetic stabilization of the lateral nuclei of the hypothalamus. In another embodiment, optogenetic stimulation to leptin-producing cells, or to cells with leptin receptors within the hypothalamus may be used to decrease appetite and hence treat obesity.

Destructive lesions to the anterior capsule and analogous DBS to that region are established means of treating severe, intractable obsessive-compulsive disorder 48 (OCD48). Such approaches may be emulated using optogenetic stabilization to the anterior limb of the internal capsule, or to regions such as BA32 and Cg24 which show metabolic decrease as OCD remits.

Chronic Pain can be treated using another embodiment of the present invention. Electrical stimulation methods include local peripheral nerve stimulation, local cranial nerve stimulation and "subthreshold" motor cortex stimulation. Reasonable optogenic approaches include optogenetic stabilization at local painful sites. Attention to promoter selection would ensure that other sensory and motor fibers would be unaffected. Selective optogenetic excitation of interneurons at the primary motor cortex also may provide effective pain relief. Also, optogenetic stabilization at the sensory thalamus, (particularly medial thalamic nuclei), periventricular grey matter, and ventral raphe nuclei, may be used to produce pain relief. In an alternative embodiment, optogenetic stabilization of parvalbumin-expressing cells targeting as targeting strategy, may be used to treat pain by decreasing Substance P production. The release of endogenous opiods may be accomplished by using optogenetic excitation to increase activity in the nucleus accumbens. In an alternative embodiment, when POMC neurons of the arcuate nucleus of the medial hypothalamus are optogenetically excited, beta endorphin are increased, providing viable treatment approaches for depression and for chronic pain.

Parkinson's Disease can be treated by expressing optogenetic stabilization in the glutamatergic neurons in either the subthalamic nucleus (STN) or the globus pallidus interna (GPi) using an excitatory-specific promoter such as CaMKIIα, and apply optogenetic stabilization. Unlike electrical modulation in which all cell-types are affected, only glutamatergic STN neurons would be suppressed.

Certain personality disorders, including the borderline and antisocial types, demonstrate focal deficits in brain disorders including "hypofrontality." Direct or indirect optogenetic excitation of these regions is anticipated to produce improvement of symptoms. Abnormal bursts of activity in the amygdala are also known to precipitate sudden, unprompted flights into rage: a symptom of borderline personality disorder, as well as other conditions, which can benefit from optogenetic stabilization of the amygdala. Optogenetic approaches could improve communication and synchronization between different parts of the brain, including amygdala, striatum, and frontal cortex, which could help in reducing impulsiveness and improving insight.

The amygdalocentric model of post-traumatic-stress disorder (PTSD) proposes that it is associated with hyperarousal of the amygdala and insufficient top-down control by the medial prefrontal cortex and the hippocampus. Accordingly, PTSD may be treated with optogenetic stabilization of the amygdale or hippocampus.

Schizophrenia is characterized by abnormalities including auditory hallucinations. These might be treated by suppression of the auditory cortex using optogenetic stabilization. Hypofrontality associated with schizophrenia might be treated with optogenetic excitation in the affected frontal regions. Optogenetic approaches could improve communication and synchronization between different parts of the brain which could help in reducing misattribution of self-generated stimuli as foreign.

Optogenetic stabilization of cells within the arcuate nucleus of the medial hypothalamus, which contain peptide products of pro-opiomelanocortin (POMC) and cocaine-and-amphetamine-regulating transcript (CART) can be used to reduce compulsive sexual behavior. Optogenetic excitation of cells within the arcuate nucleus of the medial hypothalamus which contain peptide products of pro-opiomelanocortin (POMC) and cocaine-and-amphetamine-regulating transcript (CART) may be used to increase sexual interest in the treatment of cases of disorders of sexual desire. In the treatment of disorders of hypoactive sexual desire testosterone production by the testes and the adrenal glands can be increased through optogenetic excitation of the pituitary gland. Optogentic excitation of the nucleus accumbens can be used for the treatment of anorgasmia.

The suprachiasmatic nucleus secretes melatonin, which serves to regulate sleep/wake cycles. Optogenetic excitation to the suprachiasmic nucleus can be used to increase melatonin production, inducing sleep, and thereby treating insomnia. Orexin (hypocretin) neurons strongly excite numerous brain nuclei in order to promote wakefulness. Optogentetic excitation of orexin-producing cell populations can be used to treat narcolepsy, and chronic daytime sleepiness.

Optogenetic stimulation of the supraoptic nucleus may be used to induce secretion of oxytocin, can be used to promote parturition during childbirth, and can be used to treat disorders of social attachment.

Like muscular palsies, the motor functions that have been de-afferented by a spinal cord injury may be treated with optogenetic excitation to cause contraction, and optogenetic stabilization to cause relaxation. This latter relaxation via optogenetic stabilization approach may also be used to prevent muscle wasting, maintain tone, and permit coordinated movement as opposing muscle groups are contracted. Likewise, frank spasticity may be treated via optogenetic stabilization. Re-growth of new spinal neuronal tracts may be encouraged via optogenetic excitation, which serves to signal stem cells to sprout axons and dendrites, and to integrate themselves with the network.

Stroke deficits include personality change, motor deficits, sensory deficits, cognitive loss, and emotional instability. One strategy for the treatment of stroke deficits is to provide optogenetic stimulation to brain and body structures that have been deafferented from excitatory connections. Similarly, optogenetic stabilization capabilities can be imparted on brain and body structures that have been deafferented from inhibitory connections.

Research indicates that the underlying pathobiology in Tourette's syndrome is a phasic dysfunction of dopamine transmission in cortical and subcortical regions, the thalamus, basal ganglia and frontal cortex. In order to provide therapy, affected areas are preferably first identified using techniques including functional brain imaging and magnetoencephalography (MEG). Whether specifically identified or not, optogenetic stabilization of candidate tracts may be used to suppress motor tics. Post-implantation empirical testing of device parameters reveals which sites of optogenetic stabilization, and which are unnecessary to continue.

In order to treat disorders of urinary or fecal incontinence optogenetic stabilization can be used to the sphincters, for example via optogenetic stabilization of the bladder detrussor smooth muscle or innervations of that muscle. When micturation is necessary, these optogenetic processes are turned off, or alternatively can be reversed, with optogenetic stabilization to the (external) urinary sphincter, and optogenetic excitation of the bladder detrussor muscle or its innervations. When a bladder has been deafferentated, for example, when the sacral dorsal roots are cut or destroyed by diseases of the dorsal roots such as tabes dorsalis in humans, all reflex contractions of the bladder are abolished, and the bladder becomes distended. Optogenetic excitation of the muscle directly can be used to restore tone to the detrussor, prevent kidney damage, and to assist with the micturition process. As the bladder becomes "decentralized" and hypersensitive to movement, and hence prone to incontinence, optogenetic stabilization to the bladder muscle can be used to minimize this reactivity of the organ.

In order to selectively excite/inhibit a given population of neurons, for example those involved in the disease state of an illness, several strategies can be used to target the optogenetic proteins/molecules to specific populations.

For various embodiments of the present invention, genetic targeting may be used to express various optogenetic proteins or molecules. Such targeting involves the targeted expression of the optogenetic proteins/molecules via genetic control elements such as promoters (e.g. Parvalbumin, Somatostatin, Cholecystokinin, GFAP), enhancers/silencers (e.g. Cytomaglovirus Immediate Early Enhancer), and other transcriptional or translational regulatory elements (e.g. Woodchuck Hepatitis Virus Post-transcriptional Regulatory Element). Permutations of the promoter+enhancer+regulatory element combination can be used to restrict the expression of optogenetic probes to genetically-defined populations.

Various embodiments of the present invention may be implemented using spatial/anatomical targeting. Such targeting takes advantage of the fact that projection patterns of neurons, virus or other reagents carrying genetic information (DNA plasmids, fragments, etc), can be focally delivered to an area where a given population of neurons project to. The genetic material will then be transported back to the bodies of the neurons to mediate expression of the optogenetic probes. Alternatively, if it is desired to label cells in a focal region, viruses or genetic material may be focally delivered to the interested region to mediate localized expression.

Various gene delivery systems are useful in implementing one or more embodiments of the present invention. One such delivery system is Adeno-Associated Virus (AAV). AAV can be used to deliver a promoter+optogenetic probe cassett to a specific region of interest. The choice of promoter will drive expression in a specific population of neurons. For example, using the CaMKIIa promoter will drive excitatory neuron specific expression of optogenetic probes. AAV will mediate long-term expression of the optogenetic probe for at least 1 year or more. To achieve more specificity, AAV may be pseudotyped with specific serotypes 1 to 8, with each having different trophism for different cell types. For instance, serotype 2 and 5 is known to have good neuron-specific trophism.

Another gene deliver mechanism is the use of a retrovirus. HIV or other lentivirus-based retroviral vectors may be used to deliver a promoter+optogenetic probe cassette to a specific region of interest. Retroviruses may also be pseudotyped with the Rabies virus envelope glycoprotein to achieve retrograde transport for labeling cells based on their axonal projection patterns. Retroviruses integrate into the host cell's genome, therefore are capable of mediating permanent expression of the optogenetic probes. Non-lentivirus based retroviral vectors can be used to selectively label dividing cells.

Gutless Adenovirus and Herpes Simplex Virus (HSV) are two DNA based viruses that can be used to deliver promoter+ optogenetic probe cassette into specific regions of the brain as well. HSV and Adenovirus have much larger packaging capacities and therefore can accommodate much larger promoter elements and can also be used to deliver multiple optogenetic probes or other therapeutic genes along with optogenetic probes.

Focal Electroporation can also be used to transiently transfect neurons. DNA plasmids or fragments can be focally delivered into a specific region of the brain. By applying mild electrical current, surrounding local cells will receive the DNA material and expression of the optogenetic probes.

In another instance, lipofection can be used by mixing genetic material with lipid reagents and then subsequently injected into the brain to mediate transfect of the local cells.

Various embodiments involve the use of various control elements. In addition to genetic control elements, other control elements (particularly promoters and enhancers whose activities are sensitive to chemical, magnetic stimulation, or infrared radiation) can be used to mediate temporally-controlled expression of the optogenetic probes. For example, a promoter whose transcriptional activity is subject to infrared radiation allows one to use focused radiation to fine tune the expression of optogenetic probes in a focal region at only the desired time.

According to one embodiment of the present invention, the ONI device may be used in animal models of DBS, for example in Parkinsonian rats, to identify the target cell types responsible for therapeutic effects (an area of intense debate and immense clinical importance). This knowledge alone may lead to the development of improved pharmacological and surgical strategies for treating human disease.

According to another embodiment of the present invention, genetically-defined cell types may be linked with complex systems-level behaviors, and may allow the elucidation of the precise contribution of different cell types in many different brain regions to high-level organismal functioning.

For further information, citations and background information related to implementation of the above-discussed embodiments, reference may be made to the following documents, each being fully incorporated herein by reference.

U.S. Pat. No. 6,810,285 Seizure sensing and detection using an implantable device.

U.S. Pat. No. 6,647,296 Implantable apparatus for treating neurological disorders.

U.S. Pat. No. 6,597,954 System and method for controlling epileptic seizures with spatially separated detection and stimulation electrodes.

U.S. Pat. No. 6,480,743 System and method for adaptive brain stimulation.

U.S. Pat. No. 6,473,639 Neurological event detection procedure using processed display channel based algorithms and devices incorporating these procedures.

U.S. Pat. No. 6,161,045 Method for determining stimulation parameters for the treatment of epileptic seizures.

U.S. Pat. No. 6,134,474 Responsive implantable system for the treatment of neurological disorders.

Aravanis, A. M. et al. An Optical Neural Interface: In Vivo Control of Rodent Motor Cortex with Integrated Fiberoptic and Optogenetic Technology. Journal of Neural Engineering, 2007.

Benabid A L Future strategies to restore brain functions. Conference proceedings from Medicine Meets Millennium: World Congress of Medicine and Health, 2000.

Boyden, E. S., F. Zhang, E. Bamberg, G. Nagel, and K. Deisseroth, Millisecond-timescale, genetically targeted optical control of neural activity. Nat Neurosci, 2005. 8 (9): p. 1263-8.

Deisseroth, K., G. Feng, A. K. Majewska, G. Miesenbock, A. Ting, and M. J. Schnitzer, Next-generation optical technologies for illuminating genetically targeted brain circuits. J Neurosci, 2006. 26 (41): p. 10380-6.

Greenberg B D, Malone D A, Friehs G M, Rezai A R, Kubu C S, Malloy P F, Salloway S P, Okun M S, Goodman W K, Rasmussen S A. Three-year outcomes in deep brain stimulation for highly resistant obsessive-compulsive disorder. Neuropsychopharmacology (2006) 31, 2384-2393.

Mayberg H S, Lozano A M, Voon V, McNeely H E, Seminowicz D, Hamani C, Schalb J M, Kennedy S H. Deep Brain Stimulation for Treatment-Resistant Depression. Neuron, Vol. 45, 651-660, Mar. 3, 2005, 651-660.

Schlaepfer T E, Cohen M X, Frick C, Kosel M, Brodesser D, Axmacher N, Joe A Y, Kreft M, Lenartz D, Sturm V. Deep Brain stimulation to Reward Circuitry Alleviates Anhedonia in Refractory Major Depression. Neuropsychopharmacology 2007 1-10.

Singer H S, Szymanski S, Giuliano J, Yokoi F, A. Dogan S, Brasic J R, Zhou Y, Grace A A, and Wong D F. Elevated Intrasynaptic Dopamine Release in Tourette's Syndrome Measured by PETAm J Psychiatry, August 2002; 159: 1329-1336; Van der Linden G, van Heerden B, Warwick J, Wessels C, van Kradenburg J, Zungu-Dirwayi N, Stein D J.

Functional brain imaging and pharmacotherapy in social phobia: single photon emission computed tomography before and after treatment with the selective serotonin reuptake inhibitor citalopram. Prog Neuropsychopharmacol Biol Psychiatry. 2000 April; 24 (3):419-38.

Zhang, F., L. P. Wang, E. S. Boyden, and K. Deisseroth, Channelrhodopsin-2 and optical control of excitable cells. Nat Methods, 2006. 3 (10): p. 785-92.

Zhang F, Wang L P, Brauner M, Liewald J F, Kay K, Watzke N, Wood P G, Bamberg E, Nagel G, Gottschalk A, Deisseroth K. Multimodal fast optical interrogation of neural circuitry. Nature. Vol 446 5 Apr. 2007.633-641.

Schiff N D, Giacino J T, Kalmar K, Victor J D, Baker K, Gerber M, Fritz B, Eisenberg B, O'Connor J O, Kobylarz E J, Farris S, Machado A, McCagg C, Plum F, Fins J J, Rezai A R. Behavioral improvements with thalamic stimulation after severe traumatic brain injury. Nature. Vol 448. Aug. 2, 2007 pp 600-604.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For example, such modifications include combining teachings of the various patent documents cited herein; including as just one example, combining aspects of the teaching from the teachings of above-identified application Ser. No. 11/651,422 entitled System for Optical Stimulation of Target Cells. Such a combination realizes many advantages expressly discussed in each of these patent documents. Such modifications and changes do not depart from the true spirit and scope of the present invention, which is set forth in the following claims.

What is claimed is:

1. A method for electrically stimulating a target cell of a living animal in vivo, the method comprising:
    inserting an elongated structure, having a hollow portion, into a narrow passageway in the animal such that an end of the structure is sufficiently near the target cell to deliver stimulation thereto;
    while the elongated structure is in the narrow passageway, delivering a viral vector through the hollow portion of the elongated structure, wherein the viral vector comprises a nucleotide sequence encoding a light-activatable polypeptide having at least 75% amino acid sequence identity to the ChR2 amino acid sequence set forth in SEQ ID NO:1, wherein the nucleotide sequence is operably linked to a target cell type-specific promoter, and wherein said delivering provides for expression of the light-activatable polypeptide selectively in the target cell;
    after delivering the viral vector, inserting an optical fiber through the hollow portion of the elongated structure, and
    stimulating the target cell by using the optical fiber to deliver light to the light-activatable polypeptide expressed in the target cell.

2. The method of claim 1, further comprising securing the elongated structure to a skull of the animal.

3. The method of claim 1, wherein the target cell is an excitable cell.

4. The method of claim 1, wherein the target cell is a nerve cell, a heart cell, or a muscle cell.

5. A method comprising:
    inserting an elongated structure that forms a lumen into a narrow passageway in an animal;
    introducing, after insertion and through the lumen, a viral vector comprising a nucleotide sequence encoding a light-activatable polypeptide having at least at least 75% amino acid sequence identity to the ChR2 amino acid sequence set forth in SEQ ID NO:1, wherein said introducing provides for expression of the light-activatable polypeptide in the membrane of a target nerve cell located at a selected target site within the animal, and
    introducing, into and through the lumen, an optical delivery arrangement configured for directing at least one flash of light upon the light-activatable polypeptide in the target nerve cell so as to modulate the function of the target nerve cell or surrounding cells.

6. The method of claim 5, further comprising securing the elongated structure to the animal.

7. The method of claim 1, wherein the elongated structure comprises multiple parallel optical fibers that terminate around the circumference of the elongated structure, and wherein stimulating the target cells includes activating less than all of the multiple parallel fibers.

8. The method of claim 1, further comprising the step of measuring electrical properties of the target cell using a microelectrode.

9. The method of claim 1, wherein the target cell is an electrically active cell of a sinoatrial node and wherein the stimulating of the target cell causes pacing of a heart.

10. The method of claim 1, wherein the promoter is a CaMKIIα promoter.

11. The method of claim 1, wherein the nucleotide sequence is optimized for expression in mammalian cells.

12. The method of claim 1, wherein the light-activatable polypeptide has at least 85% amino acid sequence identity to amino acid sequence set forth in SEQ ID NO:1.

13. The method of claim 1, wherein the light-activatable polypeptide has at least 95% amino acid sequence identity to amino acid sequence set forth in SEQ ID NO:1.

14. The method of claim 5, wherein the light-activatable polypeptide has at least 85% amino acid sequence identity to the amino acid sequence set forth in SEQ ID NO: 1.

15. The method of claim 5, wherein the light-activatable polypeptide has at least 95% amino acid sequence identity to the amino acid sequence set forth in SEQ ID NO:1.

16. The method of claim 1, wherein the target cell is in the anterior cingulate, the prefrontal cortex, the posterior cingulate gyrus, or a Brodmann Area.

17. The method of claim 1, wherein the viral vector is a lentiviral vector, an adenoassociated viral vector, a retroviral vector, or an adenoviral vector.

18. The method of claim 5, wherein the viral vector is a lentiviral vector, an adenoassociated viral vector, a retroviral vector, or an adenoviral vector.

19. The method of claim 1, wherein the animal is a mammal.

20. The method of claim 5, wherein the animal is a mammal.

* * * * *